US006576702B2

(12) United States Patent
Anderle et al.

(10) Patent No.: US 6,576,702 B2
(45) Date of Patent: Jun. 10, 2003

(54) PLASTICIZED WATERBORNE POLYURETHANE DISPERSIONS AND MANUFACTURING PROCESS

(75) Inventors: Gary A. Anderle, North Olmsted, OH (US); Susan L. Lenhard, Parma, OH (US); Alexander V. Lubnin, Copley, OH (US); George E. Snow, Medina, OH (US); Krishnan Tamareselvy, Brecksville, OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 0 days.

(21) Appl. No.: 09/908,045

(22) Filed: Jul. 18, 2001

(65) Prior Publication Data
US 2002/0028875 A1 Mar. 7, 2002

Related U.S. Application Data
(60) Provisional application No. 60/219,560, filed on Jul. 20, 2000.

(51) Int. Cl.$^7$ .............. C08J 3/00; C08K 3/20; C08L 75/00
(52) U.S. Cl. .......... 524/591; 524/839; 524/840
(58) Field of Search ............... 524/591, 839, 524/840

(56) References Cited

U.S. PATENT DOCUMENTS

| 2,438,091 A | 3/1948 | Lynch |
| 2,528,378 A | 10/1950 | Mannheimer |
| 2,658,072 A | 11/1953 | Kosmin |
| 3,755,560 A | 8/1973 | Dickert |
| 4,048,001 A | 9/1977 | Remley ............ 156/331 |
| 4,207,128 A | 6/1980 | Träubel et al. ......... 156/77 |
| 4,242,468 A | 12/1980 | Baack |
| 4,306,998 A | 12/1981 | Wenzel |
| 4,316,832 A | 2/1982 | Walkden |
| 4,421,769 A | 12/1983 | Dixon |
| 4,544,678 A | 10/1985 | Fesman |
| 4,704,272 A | 11/1987 | Oh |
| 4,788,006 A | 11/1988 | Bolich, Jr. |
| 5,011,681 A | 4/1991 | Ciotti |
| RE33,755 E | 11/1991 | Downey |
| RE33,761 E | 12/1991 | Brauer |
| 5,073,372 A | 12/1991 | Turner |
| 5,102,938 A | 4/1992 | Roberts |
| 5,380,528 A | 1/1995 | Alban |
| 5,599,549 A | 2/1997 | Wivell |
| 5,688,892 A | 11/1997 | Ishii |
| 5,847,040 A | 12/1998 | Tatman |
| 5,852,103 A | 12/1998 | Bhat |
| 5,874,095 A | 2/1999 | Deckner |
| 5,883,085 A | 3/1999 | Blank |
| 5,907,014 A | 5/1999 | Quint |
| 5,948,416 A | 9/1999 | Wagner |
| 6,013,271 A | 1/2000 | Doughty |
| 6,017,997 A | 1/2000 | Snow |

FOREIGN PATENT DOCUMENTS

| DE | 19812751 | 10/1999 |
| EP | 1 064 314 | 3/2001 |
| WO | WO 9816571 | 4/1998 |

OTHER PUBLICATIONS

64 Fed. Reg. 27666–27593 (May 21, 1999).

Primary Examiner—Patrick D. Niland
(74) Attorney, Agent, or Firm—Thoburn T. Dunlap; Hudak, Shunk & Farine Co. LPA; Charles A. Crehore

(57) ABSTRACT

Waterborne polyurethane dispersions are prepared by reacting (1) at least one polyisocyanate; (2) at least one active hydrogen containing compound, such as a polyol or a polyamide; and (3) preferably also at least one water-dispersability enhancing compound having water-dispersion enhancing groups, in order to form an isocyanate terminated prepolymer. The prepolymer subsequently is (1) optionally neutralized by reaction with at least one neutralizing agent, (2) dispersed in water, and then (3) chain extended by reaction with at least one of water, inorganic or organic polyamine having an average of about 2 or more primary and/or secondary amine groups, or combinations thereof. At least one plasticizer is introduced into the reaction mixture at any time during prepolymer formation or before the prepolymer is dispersed in water. The plasitcizer substantially or completely replaces other organic diluents or solvents. Various types of plasticizers may be employed, including reactive plasticizers.

94 Claims, No Drawings

PLASTICIZED WATERBORNE POLYURETHANE DISPERSIONS AND MANUFACTURING PROCESS

RELATED APPLICATION

This application claims the priority filing date of U.S. Provisional Application Ser. No. 60/219,560 filed Jul. 20, 2000.

FIELD OF THE INVENTION

This invention relates to waterborne polyurethane dispersions prepared using at least one plasticizer as a prepolymer diluent and in the substantial absence of other organic diluents or solvents. Such dispersions have higher solids and produce articles having lower modulus than articles made from dispersions prepared using a prepolymer diluent such as N-methyl-2-pyrrolidone (NMP).

BACKGROUND OF THE INVENTION

U.S. Pat. No. 6,017,997 (incorporated herein by reference) relates to waterborne polyurethanes having film properties comparable to rubber. A prepolymer is formed by reacting (1) a polyisocyanate compound; (2) an active hydrogen containing compound, such as a polyol or a polyamide; and (3) a water-dispersion enhancing compound having water-dispersion enhancing groups to form an isocyanate terminated prepolymer. The prepolymer is (1) neutralized by reaction with a tertiary amine, (2) dispersed in water, and (3) then chain extended by reaction with a primary or secondary amine. N-methyl-2-pyrrolidone (NMP) may be used as a coalescing (film forming) agent, and also as a diluent to render the viscosity of the prepolymer low enough to process it readily. However, NMP reduces the solids of the dispersion and is undesirable as a volatile organic compound (VOC) from an environmental standpoint. Excess isocyanate may also be used as a diluent but will increase the modulus of polyurethane articles made from the dispersions. Such higher modulus is undesirable for producing a "rubbery" polymer. There is no teaching of plasticizers as diluents or for any other purpose.

U.S. Pat. No. 4,306,998 relates to auxiliary agents and additives that are insoluble and not dispersible in water and are incorporated in oligo- and polyurethanes before the latter are dispersed in water. Plasticizers are among many such additives listed, but there is no suggestion that plasticizers replace diluents such as NMP. The desirability of solvent-free dispersions is mentioned, but solvents (acetone and NMP are among the compounds listed as solvents) generally are distilled off before the oligo- or polyurethane is dispersed or during or immediately after dispersion in order to obtain a solvent-free dispersion.

U.S. Pat. No. 4,316,832 relates to a plasticizer composition for synthetic resins consisting essentially of (a) the phthalate ester of an aliphatic alcohol containing from 5 to 12 carbon atoms in the aliphatic moiety, and intimately mixed therewith, (b) a polyurethane resin which is the reaction product of a di-isocyanate and a polyester based in part upon terephthalic acid. U.S. Pat. No. 4,242,468 relates to monohydroxylated polybutadienes as reactive or internal plasticizers for polyurethanes. U.S. Pat. No. 5,688,892 relates to an isocyanate-terminated prepolymer comprising the product of reaction between tolylene diisocyanate and a polyoxyethylenepropylene polyol, which is cured together with an aromatic polyamine crosslinker composed of diethyltoluenediamine and a plasticizer. There is no teaching in these three patents regarding waterborne polyurethane dispersions, nor any teaching of avoidance of traditional solvents such as NMP in the preparation of such waterborne polyurethanes.

U.S. Pat. No. 5,102,938 relates to compositions comprising a water-immiscible organic solvent or solvent blend, and a water-soluble polyurethane prepolymer having terminal isocyanate groups. Listed water-immiscible solvents include various ketones and plasticizers. The prepolymer is reactive in the presence of water to form a crosslinked, water-insoluble, water-containing gelatinous mass having a high degree of elasticity. There is no teaching of avoidance of traditional solvents such as NMP during preparation of waterborne polyurethane dispersions.

An improved polyurethane manufacturing process is desired that produces less hazardous waterborne polyurethane dispersions having higher solids, lower modulus, and other improved properties compared to polyurethanes of the prior art.

SUMMARY OF THE INVENTION

Waterborne polyurethane dispersions are prepared using a plasticizer as a prepolymer diluent in order to substantially or completely replace prior art diluents such as N-2-methyl pyrrolidone (NMP). Such dispersions are less hazardous, have higher solids and produce articles having lower modulus and other improved properties compared to articles made from dispersions prepared using the prior art prepolymer diluents.

The waterborne polyurethane dispersions are prepared by reacting (1) at least one polyisocyanate; (2) at least one active hydrogen containing compound, and (3) optionally, at least one water-dispersability enhancing compound having water-dispersability enhancing groups to form an isocyanate terminated prepolymer. The prepolymer subsequently is (1) optionally neutralized by reaction with at least one neutralizing agent, (2) dispersed in water, and then (3) chain extended by reaction with at least one of water, inorganic or organic polyamine having an average of about 2 or more primary and/or secondary amine groups, or combinations thereof. At least one plasticizer is introduced into the reaction mixture at any time during prepolymer formation or before the prepolymer is dispersed in water. The process is conducted in the substantial or complete absence of an organic solvent or a diluent other than the plasticizer.

DETAILED DESCRIPTION OF THE INVENTION

The present invention relates to waterborne polyurethane dispersions prepared by reacting (1) at least one polyisocyanate; (2) at least one active hydrogen containing compound, such as a polyol, a polyamide, or mixture thereof; and (3) optionally, at least one water-dispersability enhancing compound having water-dispersability enhancing groups, in order to form an isocyanate terminated prepolymer. The prepolymer subsequently is (1) optionally neutralized by reaction with at least one neutralizing agent, (2) dispersed in water, and (3) then chain extended by reaction with at least one of water, inorganic or organic polyamine having an average of about 2 or more primary and/or secondary amine groups, or combinations thereof. At least one plasticizer is introduced into the reaction mixture at any time during prepolymer formation or before the prepolymer is dispersed in water. The process is conducted in the substantial absence and preferably in the complete absence of an organic solvent or a diluent other than the plasticizer.

The chain-extended prepolymer compositions of the present invention are conveniently referred to as polyurethanes because they contain urethane groups. They can be more accurately described as poly(urethane/urea)s if the active hydrogen containing compound is a polyol, or as polyureas if the active hydrogen containing compound is a polyamide. It is well understood by those skilled in the art that "polyurethanes" is a generic term used to describe polymers obtained by reacting isocyanates with at least one hydroxyl-containing compound, amine containing-compound, or mixture thereof. It also is well understood by those skilled in the art that polyurethanes also include allophanate, biuret, carbodiimide, oxazolidinyl, isocynaurate, uretdione, and other linkages in addition to urethane and urea linkages.

As used herein, the term "wt. %" means the number of parts by weight of monomer per 100 parts by weight of polymer, or the number of parts by weight of ingredient per 100 parts by weight of glove, personal care, or other composition.

Polyisocyanates

Suitable polyisocyanates have an average of about two or more isocyanate groups, preferably an average of about two to about four isocyanate groups and include aliphatic, cycloaliphatic, araliphatic, and aromatic polyisocyanates, used alone or in mixtures of two or more. Diisocyanates are more preferred.

Specific examples of suitable aliphatic polyisocyanates include alpha, omega-alkylene diisocyanates having from 5 to 20 carbon atoms, such as hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, and the like. Polyisocyanates having fewer than 5 carbon atoms can be used but are less preferred because of their high volatility and toxicity. Preferred aliphatic polyisocyanates include hexamethylene-1,6-diisocyanate, 2,2,4-trimethyl-hexamethylene-diisocyanate, and 2,4,4-trimethyl-hexamethylene diisocyanate.

Specific examples of suitable cycloaliphatic polyisocyanates include dicyclohexylmethane diisocyanate, (commercially available as Desmodur™ W from Bayer Corporation), isophorone diisocyanate, 1,4-cyclohexane diisocyanate, 1,3-bis-(isocyanatomethyl) cyclohexane, and the like. Preferred cycloaliphatic polyisocyanates include dicyclohexylmethane diisocyanate and isophorone diisocyanate.

Specific examples of suitable araliphatic polyisocyanates include m-tetramethyl xylylene diisocyanate, p-tetramethyl xylylene diisocyanate, 1,4-xylylene diisocyanate, 1,3-xylylene diisocyanate, and the like. A preferred araliphatic polyisocyanate is tetramethyl xylylene diisocyanate.

Examples of suitable aromatic polyisocyanates include methane-bis-(4-phenyl isocyanate), toluene diisocyanate, their isomers, naphthalene diisocyanate, and the like. A preferred aromatic polyisocyanates is toluene diisocyanate.

The preferred diisocyanate for glove applications is an aliphatic diisocyanate. Isophorone diisocyanate (IPDI) and an isomer blend of 2,2,4- and 2,4,4-trimethyl hexamethylene diisocyanate (TMDI) are the aliphatic diisocyanates of choice for surgical gloves because of their inherent "softness" (in order to make low modulus films), lower prepolymer viscosity, and relatively high tensile strength capabilities.

Other polyisocyanates may be used in whole or in part substitution to attain similar properties, but will lessen certain polymer qualities. For example, tetramethyl xylylene diisocyanate (TMXDI) decreases tensile strength, and methylene bis-(4-cyclohexylisocyanate) ($H_{12}MDI$) and methylene bis-(4-phenylisocyanate) (MDI) increase modulus. Toluene diisocyanate (TDI) may work in the present invention if non-yellowing properties are not required. TMXDI and $H_{12}MDI$ have been found to be suitable for personal care applications where higher modulus is desired.

Active Hydrogen Containing Compounds

The term "active hydrogen containing" refers to compounds that are a source of active hydrogen and that can react with isocyanate groups via the following reaction:

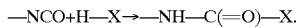

Such compounds typically range widely in molecular weight from about 50 to about 10,000 Daltons. High molecular weight compounds are preferred. The term "high molecular weight" means compounds having molecular weights from about 500 to about 10,000 Daltons, preferably about 500 to about 6,000 Daltons. Examples of suitable active hydrogen containing compounds include polyols and polyamines.

The term "polyol" denotes any high molecular weight product, typically referred to as a long-chain polyol, which has an active hydrogen that can be reacted and includes materials having an average of about two or more hydroxyl groups per molecule. Such long-chain polyols that can be used in the present invention include higher polymeric polyols such as polyester polyols and polyether polyols, as well as polyhydroxy polyester amides, hydroxyl-containing polycaprolactones, hydroxyl-containing acrylic interpolymers, hydroxyl-containing epoxies, polyalkylene ether polyols, polyhydroxy polycarbonates, polyhydroxy polyacetals, polyhydroxy polythioethers, polysiloxane polyols, ethoxylated polysiloxane polyols, polybutadiene polyols, and the like, and mixtures thereof. The polyester polyols, polyether polyols, polycarbonate polyols, polysiloxane polyols, and ethoxylated polysiloxane polyols are preferred.

The polyester polyols typically are esterification products prepared by the reaction of organic polycarboxylic acids or their anhydrides with a stoichiometric excess of a diol. Examples of suitable polyols for use in the reaction include polyglycol adipates, polyethylene terephthalate polyols, polycaprolactone polyols, orthophthalic polyols, sulfonated polyols, and the like, and mixtures thereof.

The diols used in making the polyester polyols include alkylene glycols, e.g., ethylene glycol, 1,2- and 1,3-propylene glycols, 1,2-, 1,3-, 1,4-, and 2,3-butylene glycols, hexane diols, neopentyl glycol, 1,6-hexanediol, 1,8-octanediol, and other glycols such as bisphenol-A, cyclohexane diol, cyclohexane dimethanol (1,4-bis-hydroxymethylcycohexane), 2-methyl-1,3-propanediol, 2,2,4-trimethyl-1,3-pentanediol, triethylene glycol, tetraethylene glycol, polyethylene glycol, dipropylene glycol, polypropylene glycol, dibutylene glycol, polybutylene glycol, caprolactone diol, dimerate diol, hydroxylated bisphenols, polyether glycols, halogenated diols, and the like, and mixtures thereof. Preferred diols include ethylene glycol, butylene glycol, hexane diol, and neopentyl glycol.

Suitable carboxylic acids used in making the polyester polyols include dicarboxylic acids and tricarboxylic acids and anhydrides, e.g., maleic acid, maleic anhydride, succinic acid, glutaric acid, glutaric anhydride, adipic acid, suberic acid, pimelic acid, azelaic acid, sebacic acid, chlorendic acid, 1,2,4-butane-tricarboxylic acid, phthalic acid, the isomers of phthalic acid, phthalic anhydride, fumaric acid, dimeric fatty acids such as oleic acid, and the like, and mixtures thereof. Preferred polycarboxylic acids used in making the polyester polyols include aliphatic or aromatic dibasic acids.

Preferably, the polyester polyol for making surgical gloves should be as non-crystalline as possible and in that regard should have a broad melting range and be liquid at 90° F. or lower. The average molecular weight for the polyester polyol should be at least 2400 Daltons to afford high elongation and low tensile modulus at a given elongation. The preferred molecular weight for the polyols and polyamides used in making surgical gloves is from about 2400 to about 5500 Daltons.

The preferred polyester polyol is a diol. Preferred polyester diols include hexane diol neopentyl glycol adipic acid polyester diol, e.g., Piothane 67-3000HNA (Panolam Industries) and Piothane 67-1000HNA; as well as propylene glycol maleic anhydride adipic acid polyester diols, e.g., Piothane 50-1000OPMA; and hexane diol neopentyl glycol fumaric acid polyester diols, e.g., Piothane 67-500HNF. Other preferred polyester diols include Rucoflex® S1015-35, S1040-35, and S-1040-110 (RUCO Polymer Corp.).

Polyether diols may be substituted in whole or in part for the polyester diols. Polyether polyols are obtained in known manner by the reaction of (A) the starting compounds that contain reactive hydrogen atoms, such as water or the diols set forth for preparing the polyester polyols, and (B) alkylene oxides, such as ethylene oxide, propylene oxide, butylene oxide, styrene oxide, tetrahydrofuran, epichlorohydrin, and mixtures thereof. Preferred polyethers include polypropylene glycol and copolymers of polyethylene glycol and polypropylene glycol. The use of the Acclaim® series such as Acclaim® 3201 (Arco Chemical), improved polyether diols with lower monol contents, does not reduce tensile strength significantly as would conventional polyether diols. In addition, these polyether diols give significantly lower prepolymer viscosities, which allow easier manufacture of solvent-free, low-modulus polyurethanes.

Polycarbonates include those obtained from the reaction of (A) diols such 1,3-propanediol, 1,4-butanediol, 1,6-hexanediol, diethylene glycol, triethylene glycol, tetraethylene glycol, and the like, and mixtures thereof with (B) diarylcarbonates such as diphenylcarbonate or phosgene.

Polyacetals include the compounds that can be prepared from the reaction of (A) aldehydes, such as formaldehyde and the like, and (B) glycols such as diethylene glycol, triethylene glycol, ethoxylated 4,4'-dihydroxy-diphenyldimethylmethane, 1,6-hexanediol, and the like. Polyacetals can also be prepared by the polymerization of cyclic acetals.

The aforementioned diols useful in making polyester polyols can also be used as additional reactants to prepare the isocyanate terminated prepolymer.

Instead of a long-chain polyol, a long-chain amine may also be used to prepare the isocyanate terminated prepolymer. Suitable long-chain amines include polyester amides and polyamides, such as the predominantly linear condensates obtained from reaction of (A) polybasic saturated and unsaturated carboxylic acids or their anyhydrides, and (B) polyvalent saturated or unsaturated aminoalcohols, diamines, polyamines, and mixtures thereof.

Diamines and polyamines are among the preferred compounds useful in preparing the aforesaid polyester amides and polyamides. Suitable diamines and polyamines include 1,2-diaminoethane, 1,6-diaminohexane, 2-methyl-1,5-pentanediamine, 2,2,4-trimethyl-1,6-hexanediamine, 1,12-diaminododecane, 2-aminoethanol, 2-[(2-aminoethyl)amino]-ethanol, piperazine, 2,5-dimethylpiperazine, 1-amino-3-aminomethyl-3,5,5-trimethylcyclohexane (isophorone diamine or IPDA), bis-(4-aminocyclohexyl)-methane, bis-(4-amino-3-methyl-cyclohexyl)-methane, 1,4-diaminocyclohexane, 1,2-propylenediamine, hydrazine, urea, amino acid hydrazides, hydrazides of semicarbazidocarboxylic acids, bis-hydrazides and bis-semicarbazides, diethylene triamine, triethylene tetramine, tetraethylene pentamine, pentaethylene hexamine, N,N,N-tris-(2-aminoethyl)amine, N-(2-piperazinoethyl)-ethylene diamine, N,N'-bis-(2-aminoethyl)-piperazine, N,N,N'tris-(2-aminoethyl)ethylene diamine, N-[N-(2-aminoethyl)-2-aminoethyl]-N'-(2-aminoethyl)-piperazine, N-(2-aminoethyl)-N'-(2-piperazinoethyl)-ethylene diamine, N,N-bis-(2-aminoethyl)-N-(2-piperazinoethyl)amine, N,N-bis-(2-piperazinoethyl)-amine, polyethylene imines, iminobispropylamine, guanidine, melamine, N-(2-aminoethyl)-1,3-propane diamine, 3,3'-diaminobenzidine, 2,4,6-triaminopyrimidine, polyoxypropylene amines, tetrapropylenepentamine, tripropylenetetramine, N,N-bis-(6-aminohexyl)amine, N,N'-bis-(3-aminopropyl)ethylene diamine, and 2,4-bis-(4'-aminobenzyl)-aniline, and the like, and mixtures thereof. Preferred diamines and polyamines include 1-amino-3-aminomethyl-3,5,5-trimethyl-cyclohexane (isophorone diamine or IPDA), bis-(4-aminocyclohexyl)-methane, bis-(4-amino-3-methylcyclohexyl)-methane, ethylene diamine, diethylene triamine, triethylene tetramine, tetraethylene pentamine, and pentaethylene hexamine, and mixtures thereof. Other suitable diamines and polyamines include Jeffamine® D-2000 and D-4000, which are amine-terminated polypropylene glycols, differing only by molecular weight, and which are available from Huntsman Chemical Company.

Water-dispersability Enhancing Compounds

Polyurethanes are generally hydrophobic and not water-dispersable. The water-dispersability enhancing compounds have at least one, hydrophilic, ionic or potentially ionic group whose optional presence in the polymer assists dispersion of the polyurethane in water and enhances the stability of the dispersions. Typically a compound bearing at least one hydrophilic group or a group that can be made hydrophilic (e.g., by chemical modifications such as neutralization) is incorporated into the polymer chain. For example, anionic groups such as carboxylic acid groups can be incorporated into the prepolymer in an inactive form and subsequently activated by a salt-forming compound, such as a tertiary amine defined more fully hereinafter, in order to create a prepolymer having an acid number from about 6 to about 60. Other water-dispersability enhancing compounds can also be reacted into the prepolymer backbone through urethane linkages or urea linkages, including lateral or terminal hydrophilic ethylene oxide or ureido units. The typical amount of water-dispersability enhancing compound is up to about 30 wt. %, preferably from about 2 wt. % to about 20 wt. %, and more preferably from about 2 wt. % to about 10 wt. % based on the total weight of the prepolymer.

The preferred carboxyl groups for incorporation into the isocyanate-terminated prepolymer are derived from hydroxy-carboxylic acids having the general formula (HO)$_x$Q(COOH)$_y$, wherein Q is a straight or branched hydrocarbon radical containing 1 to 12 carbon atoms, and x and y are 1 to 3. Examples of such hydroxy-carboxylic acids include citric acid, dimethylolpropanoic acid (DMPA), dimethylol butanoic acid (DMBA), glycolic acid, lactic acid, malic acid, dihydroxymalic acid, dihydroxytartaric acid, and the like, and mixtures thereof. Dihydroxy-carboxylic acids are more preferred with dimethylolproanoic acid (DMPA) being most preferred.

Other suitable water-dispersability enhancing compounds include thioglycolic acid, 2,6-dihydrooxybenzoic acid, sulfoisophthalic acid, polyethylene glycol, and the like, and mixtures thereof.

Even with use of a plasticizer as diluent, the prepolymer should be made in such a way as to minimize its resultant viscosity. The acid content of the water-dispersability enhancing compound, if present (along with ratio of NCO to active hydrogen as explained more fully below) is one consideration for producing a low viscosity prepolymer. Higher acid numbers will lead to higher viscosity. The preferred range of carboxyl containing diol or water-dispersability enhancing compound for making surgical gloves is from about 2 wt. % to about 4 wt. % of the total prepolymer, i.e., excluding plasticizer. The amount used will approach 2 wt. % as the backbone becomes more hydrophilic, as with higher concentrations of polyether diol. As the backbone becomes more hydrophobic, as with polyester based systems, the acid content needed for dispersion will approach 3–4 wt. %.

Catalysts

The formation of the isocyanate-terminated prepolymer may be achieved without the use of a catalyst. However, a catalyst is preferred in some instances. Examples of suitable catalysts include stannous octoate, dibutyl tin dilaurate, and tertiary amine compounds such as triethylamine and bis-(dimethylaminoethyl) ether, morpholine compounds such as β,β'-dimorpholinodiethyl ether, bismuth carboxylates, zinc bismuth carboxylates, iron (III) chloride, potassium octoate, potassium acetate, and DABCO® (bicycloamine) from Air Products. The preferred catalyst is FASCAT® 2003 from Elf Atochem North America. The amount of catalyst used is typically from about 5 to about 200 parts per million of the total weight of prepolymer reactants.

Plasticizers

The polyurethane is prepared in the presence of a plasticizer that acts as a diluent in order to render the viscosity of the polyurethane dispersion low enough to process it. The plasticizer can be added at any time during prepolymer preparation or before the prepolymer is dispersed in water, e.g., separately or as a mixture with one or more reaction components prior to prepolymer preparation.

Use of a plasticizer as a diluent serves a number of important functions. First, use of other diluents (such as NMP) and the like) and solvents (such as acetone and the like) is avoided or reduced, together with attendant fire, pollution and toxicity hazards of such other diluents and solvents. The plasticizer is used substantially in place of such other organic diluents and solvents, and most preferably completely in place of such other organic diluents and solvents. The maximum amount of such other organic diluents and solvents typically is less than about 20 wt. %, preferably less than about 10 wt. %, more preferably less than about 5 wt. %, and most preferably about 0 wt. % of total prepolymer weight. Furthermore, solids content of the final product is increased, since the plasticizer remains in the final product and does not require a burdensome product purification process. Moreover, intimate mixing of the plasticizer occurs, thereby avoiding or reducing problems that can occur with plasticizer addition any time after the prepolymer is dispersed in water, such as stratification and bleeding. (Stratification and bleeding can occur when a plasticizer is added following prepolymer dispersion in water; the plasticizer typically is not well mixed and separates from the composition.) Moreover, addition of plasticizer during prepolymer formation or before prepolymer dispersion in water enhances polyurethane film formation during subsequent processing to form articles such as gloves, since the intimately mixed plasticizer allows easier coalescence. Moisture resistance of the polyurethanes of this invention also is enhanced, since the intimately mixed plasticizer is hydrophobic and tends to slow hydrolysis, especially of polyester-based polyurethanes.

Plasticizers are selected for use in this invention according to parameters such as compatibility with the particular polyurethane and desired properties of the final composition. For example, polyester plasticizers tend to be more compatible with polyester-based polyurethanes. Reactive plasticizers can be used that react with functionality of the ingredients. For example, epoxy groups may be present in reactive plasticizers that react with other compounds such as aminated and hydroxylated compounds respectively. Ethylenically unsaturated groups may be present in reactive plasticizers that react with compounds having ethylenic unsaturation. Plasticizers can also be selected to impart particular properties such as flame retardancy to the polyurethanes, or to enhance particular properties such as wetting, emulsifying, conditioning, and UV absorption in end-use personal care applications. The plasticizers typically are used for gloves and personal care applications in amounts from about 5 to about 25 wt. % based on prepolymer weight. The minimum amount of plasticizer for other applications such as wood coatings, plastic coatings, textile coatings, nonwovens and paper, and the like, is determined by the desired viscosity of the prepolymer, and the optimum amount of plasticizer is determined according to the particular application, as is well known to those skilled in the art.

Suitable plasticizers include ester derivatives of such acids and anhydrides as adipic acid, azelaic acid, benzoic acid, citric acid, dimer acids, fumaric acid, isobutyric acid, isophthalic acid, lauric acid, linoleic acid, maleic acid, maleic anyhydride, melissic acid, myristic acid, oleic acid, palmitic acid, phosphoric acid, phthalic acid, ricinoleic acid, sebacic acid, stearic acid, succinic acid, 1,2-benzenedicarboxylic acid, and the like, and mixtures thereof. Also suitable are epoxidized oils, glycerol derivatives, paraffin derivatives, sulfonic acid derivatives, and the like, and mixtures thereof and with the aforesaid derivatives. Specific examples of such plasticizers include diethylhexyl adipate, heptyl nonyl adipate, diisodecyl adipate, the adipic acid polyesters sold by Solutia as the Santicizer series, dicapryl adipate, dimethyl azelate, diethylene glycol dibenzoate and dipropylene glycol dibenzoate (such as the K-Flex® esters from Kalama Chemical), polyethylene glycol dibenzoate, 2,2,4-trimethyl-1,3-pentanediol monoisobutyrate benzoate, 2,2,4-trimethyl-1,3-pentanediol diisobutyrate, methyl (or ethyl, or butyl) phthalyl ethyl glycolate, triethyl citrate, dibutyl fumarate, 2,2,4-trimethyl-1,3-pentanediol diisobutyrate, methyl laurate, methyl linoleate, di-n-butyl maleate, tricapryl trimellitate, heptyl nonyl trimellitate, triisodecyl trimellitate, triisononyl trimellitate, isopropyl myristate, butyl oleate, methyl palmitate, tricresyl phosphate, dimethyl phthalate, diethyl phthalate, dibutyl phthalate, diisobutyl phthalate, di-2-ethylhexyl phthalate, octyl decyl phthalate, diisodecyl phthalate, heptyl nonyl phthalate, diundecyl phthalate, ditridecyl phthalate, dicyclohexyl phthalate, diphenyl phthalate, butyl benzyl phthalates such as the n-butylbenzyl ester of o-phthalic acid, isodecyl benzyl phthalate, alkyl ($C_7/C_9$) benzyl phthalate, dimethoxyethyl phthalate, 7-(2,6,6,8-tetramethyl-4-oxa-3-oxo-nonyl) benzyl phthalate, di-2-ethylhexyl sebacate, butyl ricinoleate, dimethyl sebacate, methyl stearate, diethyl succinate, the butyl phenylmethyl ester of 1,2-benzenedicarboxylic acid, epoxidized linseed oil, glycerol triacetate, chloroparaffins having about 40% to about 70% Cl, o,p-toluenesulfonamide, N-ethyl p-toluene sulfonamide, N-cyclohexyl p-toluene sulfonamide, sulfonamide-formaldehyde resin, and mixtures thereof. Other suitable plasticizers known to those skilled in the art include castor oil, aromatic petroleum condensate, partially hydrogenated terphenyls, silicone plasticizers such as dimethicone copolyol esters, dimethiconol esters, silicone carboxylates, guerbet esters, and the like, alone or as mixtures with other plasticizers.

Dibenzoate esters are of particular interest in personal care applications as replacements for more hazardous components. Dibenzoate esters increase film flexibility and improve the dried film's resistance to moisture. Suitable dibenzoate esters include those set forth heretofore as well as the preferred p-aminobenzoic acid (PABA) esters, which are known to absorb UV (ultraviolet) radiation in the UVC band or region of the spectrum. UV radiation can eventually cause wrinkles, age spots, and even skin cancer.

The most damaging UV radiation can be divided into three bands: UVA, UVB, and UVC. UVA (about 320 to about 400 nm) penetrates down to the dermis and damages the skin's "elastic substances" (like sunburn or tanning). UVB (280–320 nm) typically is the most destructive form of UV radiation, believed to be the primary cause of sunburn and known to cause skin cancer. UVC (about 200 to about 280 nm) is the shortest, most energetic, and would likely be even more harmful than UVB but is largely filtered by the ozone layer and prevented from reaching the earth's surface. The UVC band is largely filtered by the ozone layer so that it does not reach the earth's surface as readily as the other two bands described below. Plasticizers can be effective in personal care products together with the sunscreens described hereafter in order to reduce radiation exposure in all UV bands.

Examples of suitable reactive plasticizers include compositions and mixtures having ethylenic unsaturation, such as triallyl trimellitate (TATM), Stepanol PD-200LV (a mixture of (1) unsaturated oil and (2) polyester diol reaction product of o-phthalic acid and diethylene glycol from Stepan Company), and the like, and mixtures thereof. Other suitable reactive plasticizers include epoxidized plasticizers, including certain monofuctional and polyfunctional glycidyl ethers such as Heloxy® Modifier 505 (polyglycidyl ether of castor oil) and Heloxy® Modifier 71 (dimer acid diglycidyl ether) from Shell Chemical Company, and the like, and mixtures thereof.

Examples of suitable flame retardant plasticizers include phosphorus-based plasticizers such as cyclic phosphates, phosphites, and phosphate esters, exemplified by Pliabrac TCP (tricresyl phosphate), Pliabrac TXP (trixylenyl phosphate), Antiblaze N (cyclic phosphate esters), Antiblaze TXP (tar acid, cresol, xylyl, phenol phosphates), and Antiblaze 524 (trixylyl phosphate) from Albright & Wilson Americas; Firemaster BZ 54 (halogenated aryl esters) from Great Lakes Chemicals; chlorinated biphenyl, 2-ethylhexyl diphenyl phosphate, isodecyl diphenyl phosphate, triphenyl phosphate, cresyl diphenyl phosphate, p-t-butylphenyl diphenyl phosphate, triphenyl phosphite, and the like. Other examples of phosphorus-based plasticizers include chlorinated alkyl phosphate esters such as Antiblaze 100 (chloro alkyl diphosphate ester) from Albright & Wilson Americas; alkyl phosphates and phosphites such as tributyl phosphate, tri-2-ethylhexyl phosphate, and triisoctyl phosphite; other organophosphates and organophosphites such as tributoxy ethylphosphate; other phosphates and phosphonates such as chlorinated diphosphate and chlorinated polyphosphonate; and the like. Mixtures can also be used.

Examples of suitable wetting, emulsifying, and conditioning plasticizers include alkyloxylated fatty alcohol phosphate esters such as oleth-2 phosphate, oleth-3 phosphate, oleth-4 phosphate, oleth-10 phosphate, oleth-20 phosphate, ceteth-8 phosphate, ceteareth-5 phosphate, ceteareth-10 phosphate, PPG ceteth-10 phosphate, and mixtures thereof.

Prepolymer Ratios of Isocyanate to Active Hydrogen

As stated above, even with use of a plasticizer as diluent, the prepolymer should be made in such a way as to minimize its resultant viscosity. In neat (no solvent) and solution polymers, viscosity is determined largely by the molecular weight of the polymer. To minimize the molecular weight of a finished prepolymer, an NCO to active hydrogen ratio of about 2/1 should be used. In this way the diol or amine portions are essentially endcapped by the diisocyanate species, leaving an isocyanate terminated prepolymer of relatively low viscosity. As the NCO to active hydrogen ratio of a prepolymer is reduced, the resultant viscosity increases dramatically. It is recognized that diluent-free materials can be made at below about 2/1 NCO to active hydrogen ratios, but they become more difficult to process, pump, stir, and the like. Also, higher temperatures will be needed to work with such a prepolymer, which increases the likelihood of undesirable side reactions.

As the NCO to active hydrogen ratio of a prepolymer is increased above about 2/1, the molecular weight will be limited as with the 2/1 ratio, but the excess diisocyanate will function as a diluent, further reducing viscosity. While this is a desired effect, raising the NCO to active hydrogen ratio above about 2/1 can also have negative effects. When isocyanate content of a polyurethane is increased, the hardness, or modulus of the polyurethane, along with the yield point, is increased. This is undesirable for producing a "rubbery" polymer. Also, when excess diisocyanate (obtained from using an NCO to active hydrogen ratio much greater than about 2/1) is introduced into a dispersion, and this dispersion is then extended with a primary (or secondary) amine, high molecular weight polyureas may be formed. These materials are not easily dispersable, but by controlling the ratio in the range of closer to about 2/1, the results will be increasingly satisfactory. If an excess of isocyanate is used, the result may be gels or grittiness in a cast film, and sediment in the dispersion. This can lead to weakened films having a poor appearance. For these reasons, NCO to active hydrogen ratios of about 1.4/1 to about 2/1 are preferred for making surgical gloves, and ratios of about 1.5/1 to about 1.8/1 are more preferred.

Prepolymer Neutralization

Optional neutralization of the prepolymer having pendant carboxyl groups converts the carboxyl groups to carboxylate anions, thus having a water-dispersability enhancing effect. Suitable neutralizing agents include tertiary amines, metal hydroxides, ammonium hydroxide, phosphines, and other agents well known to those skilled in the art. Tertiary amines are preferred and include triethyl amine (TEA), which is preferred for making surgical gloves, as well as dimethyl ethanolamine (DMEA), N-methyl morpholine, and mixtures thereof. It is recognized that primary or secondary amines may be used in place of tertiary amines, if they are sufficiently hindered to avoid interfering with the chain extension process.

Chain Extenders

As a chain extender, at least one of water, inorganic or organic polyamine having an average of about 2 or more primary and/or secondary amine groups, or combinations thereof is suitable for use in the present invention. Suitable organic amines for use as a chain extender include diethylene triamine (DETA), ethylene diamine (EDA), meta-xylylenediamine (MXDA), aminoethyl ethanolamine (AEEA), and 2-methyl pentane diamine. Also suitable for practice in the present invention are propylene diamine, butylene diamine, hexamethylene diamine, cyclohexylene diamine, phenylene diamine, tolylene diamine, 3,3-dichlorobenzidene, 4,4'-methylene-bis-(2-chloroaniline), 3,3-dichloro-4,4-diamino diphenylmethane, and mixtures thereof. Other suitable inorganic amines include hydrazine, substituted hydrazines, and hydrazine reaction products. Hydrazine is preferred and is most preferably used as a solution in water. The amount of chain extender typically ranges from about 0.5 to about 0.95 equivalents based on available isocyanate.

Polymer Branching

A degree of branching of the polymer may be beneficial, but is not required to maintain a high tensile strength and improve resistance to creep—that is, recovery to that of or near its original length after stretching. This degree of branching may be accomplished during the prepolymer step or the extension step. For branching during the extension step, the chain extender DETA is preferred, but other amines having an average of about two or more primary and/or secondary amine groups may also be used. For branching during the prepolymer step, it is preferred that trimethylol propane (TMP) and other polyols having an average of about two or more hydroxyl groups be used. When used, the branching monomers may be present in amounts from about 0.5 wt. % to about 4 wt. % of the polymer backbone. Preferably the requisite degree of branching needed is obtained during the chain extension step rather than during the prepolymer step. Otherwise, the high viscosity of the prepolymer resulting from branching may result in more difficult handling during the extension step.

Other Additives for Preparation of Dispersions

Other additives well known to those skilled in the art can be used to aid in prepartion of the dispersions of this invention. Such additives include surfactants, stabilizers, defoamers, antimicrobial agents, antioxidants, and the like.

Overview of Applications

The plasticized waterborne polyurethanes of the present invention may be useful in making rubbery articles having lower modulus than articles made without said plasticizer. Such polyurethanes have substantial amounts of both urethane and urea linkages and can be customized in a variety of ways to make polymers and products suitable for a variety of applications. For example, it typically is desirable during the manufacture of rubber-like articles (such as surgical gloves and the like by a coagulation process) to produce very soft, strong films from a solvent-free polymer. The coagulation process is well known to those skilled in the art and typically stiffens the polymer substantially, i.e., increases the polymer modulus by 50% or more. The compositions of the present invention have lower modulus than prior art polymers for such applications.

Alternatively, reactive plasticizers can be used as described heretofore to replace the plasticizers at least partially in applications where lower modulus is not important or is not as important, such as in hard, non-rubbery coatings for nails, articles such as furniture, and the like.

Additives such as activators, curing agents, stabilizers such as Stabaxol P200 and IGEPAL CO630, colorants, pigments, neutralizing agents, coagulating agents such as calcium nitrate, coalescing agents such as di(propylene glycol) methyl ether (DPM), waxes, slip and release agents, antimicrobial agents, surfactants such as Pluronic F68-LF and silicone surfactants, metals, antioxidants, UV stabilizers, antiozonants, and the like, can optionally be added as appropriate during the processing of the dispersions of this invention into finished products as is well known to those skilled in the art. Additives may be used as appropriate in order to make articles (especially flexible articles, such as gloves), or to impregnate, saturate, spray or coat papers, non-woven materials, textiles, wood, metals, polymeric articles, and a variety of other substrates. Applications include gloves; papers and non-wovens; fibrous materials such as textiles (including application to upholstery, carpets, tents, awnings, clothing, and the like); films, sheets, composites, and other articles; inks and printing binders; flock and other adhesives; and personal care products such as skin care, hair care, and nail care products; and the like.

Personal Care Applications

The waterborne polyurethane dispersions of the present invention are desirable in personal care compositions because of negative customer perceptions regarding the presence of NMP, especially in skin care products such as cosmetics. The waterborne polyurethane dispersions can be used as film formers in personal care formulations to provide desirable properties such as the following: water or moisture resistance, luster, better spreadability of sunscreen actives, and the like. Such dispersions can be incorporated into personal care products such as daily skin care products (cosmetics, lip balms, moisturizers, eye-lash liners, lipsticks, lip balms, sunscreens, and the like), as well as nail care products, hair care products, and the like. Such personal care products can be lotions, gels, sprays, sticks, compressed liquids, liquid suspensions, and the like.

Personal care compositions can include the waterborne polyurethane dispersions of this invention, mixed and optionally reacted further with a topically acceptable phase. The term "topically acceptable phase" means any combination of optional liquid or solid ingredients suitable for a desired personal care composition in combination with (and sometimes reacted with) the plasticized waterborne polyurethane dispersions described hereftofore. Such optional ingredients can comprise one or more of a wide variety of components well known to those skilled in the art, such as chelators, conditioners, diluents, fragrances, humectant skin or hair conditioners, lubricants, moisture barriers/ emollients, neutralizers, opacifiers, pharmaceutical actives, preservatives, solvents, spreading aids, sunscreens, surfactants, conditioning polymers, vitamins, viscosity modifiers/emulsifiers, and the like, as well as numerous other optional components for enhancing and maintaining the properties of the personal care compositions. Exemplary skin care compositions utilizing such components include those of U.S. Pat. Nos. 5,073,372, 5,380,528, 5,599,549, 5,874,095, 5,883,085, 6,013,271, and 5,948,416, all incorporated herein by reference. Such components are also described in detail in well known references such as Mitchell C. Schlossman, *The Chemistry and Manufacture of Cosmetics,* Volumes I and 11, Allured Publishing Corporation, 2000.

Suitable chelators include EDTA (ethylene diamine tetraacetic acid) and salts thereof such as disodium EDTA, citric acid and salts thereof, cyclodextrins, and the like, and mixtures thereof. Such suitable chelators typically comprise about 0.001 wt. % to about 3 wt. %, preferably about 0.01 wt. % to about 2 wt. %, and more preferably about 0.01 wt. % to about 1 wt. % of the total weight of the personal care compositions of the present invention.

A diluent such as water (often deionized) can be used and typically comprises about 5 wt. % to about 99 wt. %, and preferably about 20 wt. % to about 99 wt. % of the total weight of the personal care compositions of the present invention.

Suitable humectant skin and/or hair conditioners include allantoin; pyrrolidonecarboxylic acid and its salts; hyaluronic acid and its salts; sorbic acid and its salts; urea; lysine, arginine, cystine, guanidine, and other amino acids; polyhydroxy alcohols such as glycerin, propylene glycol, hexylene glycol, hexanetriol, ethoxydiglycol, dimethicone copolyol, and sorbitol, and the esters thereof; polyethylene glycol; glycolic acid and glycolate salts (e.g. ammonium and quaternary alkyl ammonium); lactic acid and lactate salts (e.g. ammonium and quaternary alkyl ammonium); sugars and starches; sugar and starch derivatives (e.g. alkoxylated glucose); D-panthenol; lactamide monoethanolamine; acetamide monoethanolamine; and the like, and mixtures thereof. Preferred humectants include the $C_3$–$C_6$ diols and triols, such as glycerin, propylene glycol, hexylene glycol, hexanetriol, and the like, and mixtures thereof. Such suitable humectants typically comprise about 1 wt. % to about 10 wt. %, preferably about 2 wt. % to about 8 wt. %, and more preferably about 3 wt. % to about 5 wt. % of the total weight of the personal care compositions of the present invention.

Suitable lubricants include volatile silicones, such as cyclic or linear polydimethylsiloxanes, and the like. The number of silicon atoms in cyclic silicones preferably is from about 3 to about 7 and more preferably 4 or 5. Exemplary volatile silicones, both cyclic and linear, are available from Dow Corning Corporation as Dow Corning 344, 345 and 200 fluids; Union Carbide as Silicone 7202 and Silicone 7158; and Stauffer Chemical as SWS-03314.

The linear volatile silicones typically have viscosities of less than about 5 cP at 25° C., while the cyclic volatile silicones typically have viscosities of less than about 10 cP at 25° C. "Volatile" means that the silicone has a measurable vapor pressure. A description of volatile silicones can be found in Todd and Byers, "Volatile Silicone Fluids for Cosmetics", *Cosmetics and Toiletries,* Vol. 91, January 1976, pp. 27–32, incorporated herein by reference. Other suitable lubricants include polydimethylsiloxane gums, aminosilicones, phenylsilicones, polydimethyl siloxane, polydiethylsiloxane, polymethylphenylsiloxane, polydimethylsiloxane gums, polyphenyl methyl siloxane gums, amodimethicone, trimethylsiloxyamodimethicone, diphenyl-dimethyl polysiloxane gums, and the like. Mixtures of lubricants can also be used. Such suitable lubricants typically comprise about 0.10 wt. % to about 15 wt. %, preferably about 0.1 wt. % to about 10 wt. %, and more preferably about 0.5 wt. % to about 5 wt. % of the total weight of the personal care compositions of the present invention.

Suitable moisture barriers and or emollients include mineral oil; stearic acid; fatty alcohols such as cetyl alcohol, cetearyl alcohol, myristyl alcohol, behenyl alcohol, and lauryl alcohol; cetyl acetate in acetylated lanolin alcohol, isostearyl benzoate, dicaprylyl maleate, caprylic and capric triglyceride; petrolatum, lanolin, coco butter, shea butter, beeswax and esters there of; ethoxylated fatty alcohol esters such as ceteareth-20, oleth-5, and ceteth-5; avocado oil or glycerides; sesame oil or glycerides; safflower oil or glycerides; sunflower oil or glycerides; botanical seed oils; volatile silicone oils; non-volatile emollients, and the like, and mixtures thereof. Suitable non-volatile emollients include fatty acid and fatty alcohol esters, highly branched hydrocarbons, and the like, and mixtures thereof. Such fatty acid and fatty alcohol esters include decyl oleate, butyl stearate, myristyl myristate, octyldodecyl stearoylstearate, octylhydroxystearate, di-isopropyl adipate, isopropyl myristate, isopropyl palmitate, ethyl hexyl palmitate, isodecyl neopentanoate $C_{12}$–$C_{15}$ alcohol benzoate, diethyl hexyl maleate, PPG-14 butyl ether and PPG-2 myristyl ether propionate, cetearyl octanoate, and the like, and mixtures thereof. Suitable highly branched hydrocarbons include isohexadecane and the like, and mixtures thereof. Such suitable moisture barriers and/or emollients, alone or in combination, typically comprise about 1 wt. % to about 20 wt. %, preferably about 2 wt. % to about 15 wt. %, and more preferably about 3 wt. % to about 10 wt. % of the total weight of the personal care compositions of the present invention.

Suitable neutralizers include triethanolamine, aminomethyl propanol, ammonium hydroxide, sodium hydroxide, other alkali hydroxides, borates, phosphates, pyrophosphates, cocamine, oleamine, diisopropanolamine, diisopropylamine, dodecylamine, PEG-15 cocamine, morpholine, tetrakis(hydroxypropyl)ethylenediamine, triamylamine, triethanolamine, triethylamine, tromethamine (2-Amino-2-Hydroxymethyl-1,3-propanediol, and the like, and mixtures thereof. Such suitable neutralizers typically comprise about 0 wt. % to about 3 wt. %, preferably about 0.01 wt. % to about 2 wt. %, and more preferably about 0.1 wt. % to about 1 wt. % of the total weight of the personal care compositions of the present invention.

Suitable opacifiers include glycol fatty acid esters; alkoxylated fatty acid esters; fatty acid alcohols; hydrogenated fatty acids, waxes and oils; kaolin; magnesium silicate; titanium dioxide; silica; and the like, and mixtures thereof. Such suitable opacifiers typically comprise about 0.1 wt. % to about 8 wt. %, preferably about 0.5 wt. % to about 6 wt. %, and more preferably about 1 wt. % to about 5 wt. % of the total weight of the personal care compositions of the present invention.

Suitable pharmaceutical actives useful in the present invention include any chemical substance, material or compound suitable for topical administration to induce any desired local or systemic effect. Such actives include, but are not limited to antibiotics, antiviral agents, analgesics (e.g. ibuprofen, acetyl salicylic acid, naproxen, and the like), antihistamines, anti-inflammatory agents, antipruritics, antipyretics, anesthetic agents, diagnostic agents, hormones, antifungals, antimicrobials, cutaneous growth enhancers, pigment modulators, antiproliferatives, antipsoriatics, retinoids, anti-acne medicaments (e.g. benzoyl peroxide, sulfur, and the like), antineoplastics agents, phototherapeutic agents, and keratolytics (e.g. resorcinol, salicylic acid, and the like), and the like, and mixtures thereof. Such pharmaceutical actives typically comprise about 0.1 wt. % to about 20 wt. % of the total weight of the personal care compositions of the present invention.

Suitable preservatives include polymethoxy bicyclic oxazolidine, methylparaben, propylparaben, ethylparaben, butylparaben, benzoic acid and the salts of benzoic acid, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, sorbic acid, salicylic acid salts, and the like, and mixtures thereof. Such suitable preservatives typically comprise about 0.01 wt. % to about 1.5 wt. %, preferably about 0.1 wt. % to about 1 wt. %, and more preferably about 0.3 wt. % to about 1 wt. % of the total weight of the personal care compositions of the present invention.

Suitable spreading aids include hydroxypropyl methylcellulose, hydrophobically modified cellulosics, xanthan gum, cassia gum, guar gum, locust bean gum, dimethicone copolyols of various degrees of alkoxylation, boron nitride, talc, and the like, and mixtures thereof. Such suitable spreading aids typically comprise about 0.01 wt. % to about 5 wt. %, preferably about 0.1 wt. % to about 3 wt. %, and more preferably about 0.1 wt. % to about 2.0 wt. % of the total weight of the personal care compositions of the present invention.

Suitable sunscreens can be used in safe and photoprotectively effective amounts in the personal care compositions of the present invention. Suitable sunscreens include those set forth in Segarin et al., *Cosmetics Science and Technology*, at Chapter VIII, pages 1890 et. seq., as well as 64 Fed. Reg. 27666–27693 (May 21, 1999). Specific suitable sunscreening agents include, for example, p-aminobenzoic acid and its salts and derivatives (ethyl, isobutyl, glyceryl esters; p-dimethylaminobenzoic acid; 2-ethylhexyl-N,N-dimethylaminobenzoate); anthranilates (i.e., o-aminobenzoates; methyl, octyl, amyl, menthyl, phenyl, benzyl, phenylethyl, linalyl, terpinyl, and cycohexenyl esters); salicylates (octyl, amyl, phenyl, benzyl, menthyl, glyceryl, and dipropyleneglycol esters); cinnamic acid derivatives (ethylhexyl-p-methoxy; menthyl and benzyl esters, phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenyl quinoline); hydroxymethoxy-substituted benzophenones; uric and vilouric acids; tannic acid and its derivatives (e.g. hexaethylether); (butyl carbityl) (6-propyl piperonyl) ether; hydroquinone; benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; octocrylene; 4-isopropyl-dibenzoylmethane; and camphor derivatives such as methylbenzylidene or benzylidene camphor; and the like, and mixtures thereof. Other sunscreens include the inorganic sunblocks such as titanium dioxide (micronized titanium dioxide, 0.03 microns), zinc oxide, silica, iron oxide and dioxide, and the like, and mixtures thereof with one another and with the aforementioned organic sunscreens. Without being limited by theory, it is believed that these inorganic materials provide a sunscreening benefit through reflecting, scattering, and absorbing harmful UV, visible, and infrared radiation. Particularly useful are the sunscreens ethylhexyl-p-methoxycinnamate, octyl salicylate and benzophenone, either alone, as a mixture, or in combination with the physical sunscreen titanium dioxide.

By "safe and photoprotectively" is meant an amount of sunscreen sufficient to provide photoprotection when the composition is applied, but not so much as to cause any side effects such as skin reactions. Suitable sunscreens typically comprise about 0.5 wt. % to about 50 wt. %, preferably about 0.5 wt. % to about 30 wt. %, and more preferably about 0.5 wt. % to about 20 wt. % of the total weight of the skin care compositions of the present invention. Exact amounts will vary depending upon the sunscreen chosen and the desired Sun Protection Factor (SPF).

SPF is a commonly used measure of photoprotection of a sunscreen against erythema. This number is derived from another parameter, the minimal erythemal dose (MED). MED is defined as the least exposure dose at a specified wavelength that will elicit a delayed erythema response. The MED indicates the amount of energy reaching the skin and the responsiveness of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to the same person with unprotected skin) before that person will experience 1 MED. For example, utilizing a sunscreen with an SPF of 6 will allow an individual to stay in the sun six times longer before receiving MED. As the SPF value of a sunscreen increases, a lesser chance exists for development of tanning of the skin. Commercially available sunscreening products have SPF values ranging from 2 to 50.

Suitable surfactants include a wide variety of nonionic, cationic, anionic, and zwitterionic surfactants, such as those disclosed in *McCutcheon's Detergents and Emulsifiers*, North American Edition (1986), Allured Publishing Corporation; and in U.S. Pat. Nos. 3,755,560, 4,421,769, 4,704,272, 4,741,855, 4,788,006, and 5,011,681. Examples of suitable surfactants include silicone esters, alkyl and alkenyl sulfates; alkyl and alkenyl ethoxylated sulfates (preferably having an average degree of ethoxylation from 1 to about 10); succinamate surfactants such as alkylsulfosuccinamates and dialkyl esters of sulfosuccinic acid; neutralized fatty acid esters of isethionic acid; and alkyl and alkenyl sulfonates, such as olefin sulfonates and beta-alkoxy alkane sulfonates; and the like. Preferred are alkyl and alkenyl sulfates and alkyl and alkenyl ethoxylated sulfates, such as the sodium and ammonium salts of $C_{12}$–$C_{18}$ sulfates and ethoxylated sulfates with a degree of ethoxylation from 1 to about 6, and more preferably from 1 to about 4, such as lauryl sulfate and laureth (3.0) sulfate sodium 3-dodecylaminopropionate; N-alkyltaurines such as prepared by reacting dodecylamine with sodium isethionate according to the teaching of U.S. Pat. No. 2,658,072; N-higher alkyl aspartic acids such as produced according to the teaching of U.S. Pat. No. 2,438,091; and the products sold under the trade name "Miranol" and described in U.S. Pat. No. 2,528,378; and the like. Other suitable surfactants include alkyl (preferably $C_6$–$C_{22}$ and more preferably $C_8$–$C_{12}$) amphoglycinates; alkyl (preferably $C_6$–$C_{22}$ and more preferably $C_8$–$C_{12}$) amphopropionates; and the like. Mixtures can also be used.

Suitable zwitterionic surfactants for use in the present compositions include those broadly described as derivatives of aliphatic quaternary ammonium, phosphonium, and sulfonium compounds, wherein which the aliphatic radicals can be straight chain or branched, and wherein one of the aliphatic substituents contains from about 8 to about 18 carbon atoms and another substituent contains an anionic water-dispersability enhancing group, such as carboxy, sulfonate, sulfate, phosphate, phosphonate, and the like. Classes of zwitterionics include alkyl amino sulfonates, alkyl betaines and alkyl amido betaines, stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles ethylene oxide) stearylamine, dihydroxy ethyl stearylamine, arachidylbehenylamine, and the like. Mixtures can also be used. Such suitable surfactants typically comprise about 0.1 wt. % to about 25 wt. %, preferably about 0.5 wt. % to about 25 wt. %, and more preferably about 1 wt. % to about 15 wt. % of the total weight of the personal care compositions of the present invention.

Suitable viscosity adjusters include isopropyl alcohol, ethanol, sorbitol, propylene glycol, diethylene glycol, triethylene glycol, dimethyl ether, butylene glycol, and the like, and mixtures thereof. Such suitable viscosity adjusters typically comprise about 0.1 wt. % to about 60 wt. %, preferably about 1 wt. % to about 40 wt. %, and more preferably about 5 wt. % to about 20 wt. % of the total weight of the personal care compositions of the present invention.

Skin conditioning polymers include quaternized guar gum, quaternized cellulosics, polyquaternium 4, polyquaternium 7, polyquaternium 10, polyquaternium 11, polyquaternium 39, polyquaternium 44, and the like, and mixtures thereof. Such suitable conditioning agents typically comprise about 0.1 wt. % to about 3 wt. %, preferably about 0.1 wt. % to about 2 wt. %, and more preferably about 0.1 wt % to about 0.5 wt. % of the total weight of the skin care compositions of the present invention.

Various vitamins also can be included in the compositions of the present invention. Suitable vitamins include vitamin A, vitamin B, biotin, pantothenic acid, vitamin C, vitamin D, vitamin E, tocopherol acetate, retinyl palmitate, magnesium ascorbyl phosphate, and the like, and derivatives and mixtures thereof.

Suitable viscosity modifiers/emulsifiers include natural, semi-synthetic, and synthetic polymers. Examples of natural and modified natural polymers include xanthan gums, cellulosics, modified cellulosics, starches, polysaccharides, and the like. Examples of synthetic polymers include crosslinked polyacrylates, alkali swellable emulsion acrylate copolymers, hydrophobically modified alkali swellable copolymers, hydrophobically modified non-ionic polyurethanes, and the like. Mixtures can also be used. Such suitable viscosity modifiers/emulsifiers, alone or in combination, typically comprise about 0.1 wt. % to about 5 wt. %, preferably about 0.3 wt. % to about 3 wt. %, and more preferably about 0.5 wt. % to about 2 wt. % of the total weight of the personal care compositions of the present invention.

Other optional components can be used in order to maintain and enhance the properties of personal care compositions. Such optional components include various antioxidants, agents suitable for aesthetic purposes, such as fragrances, pigments, and colorings, and the like.

The following examples are presented for the purpose of illustrating the invention disclosed herein in greater detail. However, the examples are not to be construed as limiting the invention herein in any manner, the scope of the invention being defined by the appended claims.

EXAMPLES

Chemicals Used in Examples

AEEA=aminoethyl ethanolamine from Aldrich Chemical Co., Inc.
AMP-95=aminomethyl propanol from Angus
Antiblaze N=cyclic phosphate esters from Albright & Wilson Americas
Antiblaze TCP=tar acid, cresol, xylyl, phenol phosphates from Albright & Wilson Americas
Antiblaze 100=chloro alkyl diphosphate ester from Albright & Wilson Americas
Antiblaze 524=trixylyl phosphate from Albright & Wilson
Carbopol® Ultrez™ 10 from Noveon™, Inc.
Carbopol® 980 from Noveon™, Inc.
Crovol™ A-40=PEG-20 almond glycerides from Croda
DBA=dibutylamine from Air Products and Chemicals
DeeFo XHD-47J from Ultra Additives Inc.
Dehydran 1293=modified polysiloxane from Henkel
Desmodur W=methylene bis-(4-cyclohexyl isocyanate) from Bayer Corporation
Dimethicone copolyol from Dow Corning®
Disodium EDTA=disodium ethylenediamine tetraacetic acid from Dow Chemical
DMEA=dimethylethanolamine from Aldrich Chemical Co., Inc.
DMPA=dimethylol propanoic acid from Geo Specialty Chemicals Inc.
DOWFAX 2A1=disodium (dodecyl sulfophenoxy) benzenesulfonic acid from Dow Chemical
DPM=di(propylene glycol) methyl ether from Dow Chemical
Drakeol 21=mineral oil from Penreco
Ethylenediamine from Aldrich Chemical Co., Inc.
FASCAT 2003=2-ethyl hexanoic acid and stannous octoate from Elf Atochem North America
Firemaster BZ 54=halogenated aryl ester from Great Lakes Chemicals
Fragrance #99189 "Twister" from Drom
HCl=hydrochloric acid from J. T. Baker
Hydrazine=35 wt. % solution in water from Bayer Corporation
IGEPAL CO630=branched nonylphenoxypoly(ethyleneoxy) ethanol
IPDI=isophorone diisocyanate from Bayer Corporation.
K-Flex® DE=diethylene glycol dibenzoate ester from Noveon, Inc.
K-Flex® DP=dipropylene glycol dibenzoate ester from Noveon, Inc.
K-Flex® 500=blend of K-Flex® DE and K-Flex® DP from Noveon, Inc.
Luviskol® VA64=film forming copolymer of vinyl pyrrolidone and vinyl acetate from BASF Methocel® E4M=hydroxypropyl methyl cellulose from Dow Chemical
Neo Helipan™ Type AV=octyl methoxy cinnamate from Haarmann & Reimer
Neo Helipan™ Type BB=oxybenzone from Haarmann & Reimer
NeXXus® Styling Gel™ Regular Hold from NeXXus Products Company
Nuosept™ C=polymethoxy bicyclic oxazolidine from Huls
NMP=N-methyl-2-pyrrolidone from BASF
Octyl salicylate from Noveon®, Inc.
Paul Mitchell® Style (Extra-Body Sculpting Gel®) Maximum Hold with Body from John Paul Mitchell Systems
Pemulen® TR-2 from Noveon™, Inc.
Pluronic F68-LF from BASF
PPG-1025=polypropylene glycol (average MW=1025) from Bayer Corporation
PPG-2025=polypropylene glycol (average MW=2025) from Bayer Corporation
Santicizer 160=1,2-benzenedicarboxylic acid, butyl phenylmethyl ester; and o-phthalic acid, n-butyl benzyl ester from Solutia
SLS=sodium lauryl sulfate
S1040-35=polyester diol having a molecular weight of about 3000 from Ruco Polymer Corp.
S1040-110=polyester diol having a molecular weight of about 1000 from Ruco Polymer Corp.
Stabaxol P200=aromatic polycarbodiimide from Rhein Chemie
STEPANOL PD-200LV=mixture of (1) unsaturated oil and (2) polyester diol reaction product of o-phthalic acid and diethylene glycol from Stepan Company
TATM=triallyl trimellitate from The CP Hall Company
TEA=triethylamine from Air Products and Chemicals
TMDI=approximately a 50/50 blend of 2,2,4- and 2,4,4-trimethylhexamethylene-1,6-diisocyanate from Creanova, Inc.
TMP=trimethylolpropane from Celanese
TMXDI=tetramethylxylylene diisocyanate from Cytec Industries, Inc.
Triethanolamine (99 wt. % solution in water) from Angus
Piothane® 50-1000PMA=polyester diol reaction product of propylene glycol, maleic anyhydride, and adipic acid (average MW=1000) from Panolam Industries
Piothane® 67-1000HNA=polyester diol reaction product of hexane diol, neopentyl glycol, and adipic acid (average MW=1000) from Panolam Industries
Piothane® 67-3000HNA=polyester diol reaction product of hexane diol, neopentyl glycol, and adipic acid (average MW=3000) from Panolam Industries
Piothane® 67-500HNF=polyester diol reaction product of hexane diol, neopentyl glycol, and fumaric acid (average MW=500) from Panolam Industries
Piothane® 1000-DEA=diethylene glycol apidate (average MW=1,000)

Test Methods

1. Tensile strength, modulus and % elongation testing for Examples 1–5: A glove mold is dipped into a coagulant solution, which contains calcium nitrate at a concentration of from about 2 to about 25%. The coagulant solution may also contain surfactants, thickeners, fillers, and other materials well known to those skilled in the art. The glove mold then is dried from about 1 minute to about 10 minutes at temperatures from about 20° C. to about 120° C., forming a thin layer of powder on the surface of the glove mold. The mold then is dipped into the plasticized polyurethane latex and withdrawn slowly, forming a firm, wet gel on the glove mold. The gel is dried for about 1 to about 20 minutes at about 20–120° C. in order to drive off most of the water from the wet gel. The glove then is cured at about 120–160° C. for a time of about 6 minutes to about 30 minutes. After curing, the glove is stripped off the mold and allowed to cool overnight. Tensile testing is run the following day, using dumbbells cut to 1.5" in length, and 0.188" at the center. The starting gauge length is 0.75" and the jaw speed of the pulls is 20" per minute. Room temperature is 20–25° C., and relative humidity is 30–80%.

2. Tensile strength, modulus, and % elongation testing for Examples 20–22: Each of the plasticized polyurethane dispersions of Examples 20–22 was diluted with 4% propylene glycol as a coalescing agent and then was drawn down on Mylar® film made from polyethylene terephthalate. (Examples 27–28 were prepared in the same way but without use of coalescing agent.) The Mylar® film was attached to the glass by wetting the glass with DI (deionized) water and then applying the Mylar® film to the glass with pressure using a squeegee on top with a little DI water spray underneath. If no air bubbles were seen through the Mylar® film, then the attachment was complete. The film then was washed with DI water and dried with lint-free paper. The polyurethane test film was prepared by using a 10 mil. draw down bar to apply the polyurethane dispersion to the Mylar® film. After casting the polyurethane test film, it was thoroughly dried at ambient temperature in a dust-free box. The Mylar® film and polyurethane film cast on it then were dried at 300° F. for 3 minutes in an oven. Samples were stored for 24 hours at 50% humidity and 72° F. in a temperature-conditioned room to equilibrate before testing. The Mylar® film with dried polyurethane film on it then was cut into 1-inch wide strips. The dried polyurethane film was removed from the Mylar® film. The following polyurethane film parameters were measured: width (in)=1.000; thickness (inch)=0.0016 to 0.0037; and spec gauge length (inch)=1.000. ASTM D882-95a tensile testing was performed using an Instron to measure various properties such as tensile strength, % elongation, and 100% modulus at break using these machine parameters: sample rate (pts/sec)=10; and crosshead speed in/min)=2.

3. Cracking/Splitting: The gloves are produced as test method 1 above. A visual inspection is made and any cracking or splitting of the gloves is noted.

4. Isopropanol resistance: The gloves are produced as in test method 1 above. A finger on a finished glove is stretched by hand to about 200% elongation. Two drops of Sterillium® disinfectant/antimicrobial handrinse are applied to the stretched glove finger. Gloves are rated for tearing/breaking, weakening, or severe tackiness. Gloves rated "good" do not tear, and show little-no tackiness or weakening.

5. Spectroscopic Analysis: UV spectroscopic analysis is used to characterize sunscreen chemicals, which, by definition, are UV radiation absorbers. Spectra were measured over the range of 200–450 nm using a Perkin-Elmer Lambda 9 UV-Visible spectrophotometer. The light source for the UV region was a deuterium lamp, and the source for the visible region was a tungsten-halogen lamp. The slit width was 2 nm, and the scanning speed was 240 nm/min.

UV spectrum analysis parameters that aid identification and characterization of sunscreen active chemicals include the UV pattern, the wavelength of maximum absorption ($\lambda_{max}$), and the absorbency value (or absorbence). The wavelength of maximum absorption is characteristic of the sunscreen chemical under investigation for a given solvent system. The absorbance is characteristic of the sunscreen chemical and dependent on the wavelength of light, nature of solvent, concentration, and temperature. The UV patterns of plasticized and plasticizer-free samples were recorded in ethanol at a concentration of 0.013 wt. % of the material being tested. The presence of benzoate ester plasticizer produced an additional absorption peak at 232 nm. A transmittance spectrum sample was prepared by coating a thin uniform layer of the sunscreen composition to be tested onto one face of an UV cuvette having a 5.38 cm² surface area. Preferred sunscreen lotions or other compositions have transmittances less than about 30% (or absorbences greater than about 70%).

6. Curl Retention.

Swatches of European, brown or black virgin hair supplied by International Hair Importers and Products Inc., New York were used in this test. Each hair swatch weighed about 3 grams, was about 7 inches long, and was glued together at the root ends. Each hair swatch was washed with a dilute solution of daily cleansing shampoo (10 wt. % SLS solution) followed by rinsing with deionized water at ambient temperature. About 0.8 gram of the hair styling gel being tested was applied to each hair swatch, which was then wrapped around a 3-cm hair curler. The hair was allowed to dry overnight at room temperature (about 71–73° F.). The curler then was removed, and the hair swatches were placed in a humidity chamber at 80° F. and 90 percent relative humidity in order to measure % curl retention. The opening of the curl droop was measured periodically, and a final reading was taken after 24 hours.

The % curl retention was calculated using the following formula:

% curl retention=100−{[($L_t$−$L_i$)/$L_e$]×100}, wherein $L_i$ is the length of the hair initially after curling, $L_t$ is the length of the opened curled hair after exposure to humidity, and $L_e$ is the length of the hair fully extended before curling. Satisfactory curl retention typically is at least 70% curl retention for at least 2 hours at 90% relative humidity.

Example 1

Prepolymer Step

The following materials were charged to a reactor: 1980 grams (1.31 equivalent) S1040-35 and 27 grams (0.05 equivalent) S1040-110; then with mixing, 484 grams (4.61 equivalent) TMDI and 62 grams (0.56 equivalent) IPDI were charged. Heat was applied to the batch to bring the temperature to over 190° F. After 2 hours, 87 grams (1.31 equivalent) DMPA was added, and the batch was held at over 190° F. for approximately an additional 2 hours. The % NCO remaining then was measured using a titration with DBA and 1.0 M HCl, and was found to be 3.56%. Next, 660 grams (to a total of 20 wt. % plasticizer in the prepolymer) Santicizer 160 was added to the batch, and the batch then was allowed to cool to 173° F. 72 grams TEA was charged to the batch and was allowed to mix for about 10 minutes.

Extension Step

A portion (3066 grams) of this completed, neutralized prepolymer then was charged slowly, with mixing, into 2941 g water (at 80° F.), which contained 30 grams Pluronic F68-LF surfactant, over the course of about 25 minutes, thus forming an NCO-terminated prepolymer dispersion. To this dispersion, 122 grams was added of a 50/50 mixture of Stabaxol P200 and water. Chain extension was accomplished by adding 21 grams of a 50/50 blend of AEEA and water, and then 56 grams of 35 wt. % hydrazine solution.

Example 2

Prepolymer Step

The following materials were charged to a reactor: 2227 grams (1.47 equivalent) S1040-35 and 30 grams (0.06 equivalent) S1040-110; then with mixing, 545 grams TMDI (5.19 equivalent); and 70 grams of IPDI (0.63 equivalent). Heat was applied to the batch to bring the temperature to over 190° F. After about 2 hours, 330 grams Santicizer 160 (to 10% total plasticizer in the prepolymer) and 98 grams DMPA (1.5 equivalent) were added with mixing, and the prepolymer was allowed to react for approximately 2 additional hours at over 190° F. The % NCO remaining then was measured, and was found to be 3.36%. The batch was cooled to 185° F. 82 grams TEA was charged to the batch and was allowed to mix for about 10 minutes.

Extension Step

A portion (3074 grams) of this completed, neutralized prepolymer was then charged slowly into 2828 grams water (at 79° F.), which contained 15 grams Pluronic F68-LF surfactant, over the course of about 40 minutes, thus forming an NCO terminated prepolymer dispersion. Then 6 grams DeeFo XHD-47J defoamer was added to the dispersion, followed by 77 grams of 35 wt. % hydrazine solution (for chain extension), and 150 grams of an 80/20 mixture of water/Stabaxol P200.

Example 3

Prepolymer Step

The following materials were charged to a reactor: 2211 grams (1.46 equivalent) S1040-35 and 30 grams (0.06 equivalent) S1040-110; then with mixing, 516 grams (4.91 equivalent) TMDI and 50 grams (0.45 equivalent) IPDI. Heat was applied to the batch to bring the temperature to over 190° F. After about 2 hours, 98 grams (1.5 equivalent) DMPA and 198 grams Santicizer 160 were added with mixing, and the prepolymer was allowed to react for approximately 2 additional hours at over 190° F. The % NCO remaining then was measured and found to be 2.82%. The batch was cooled to 178° F. TEA (81 grams) was charged to the batch and was allowed to mix for about 10 minutes.

Extension Step

A portion (3074 grams) of this completed, neutralized prepolymer then was charged slowly into 2848 grams water (at 76° F.), which contained 30 grams Pluronic F68-LF surfactant, over the course of about 40 minutes, thus forming an NCO terminated prepolymer dispersion. About halfway through the dispersion, 6 grams DeeFo XHD-47J defoamer was added. After about 40 minutes mixing, 61 grams 35 wt. % hydrazine solution was added slowly to the dispersion (for chain extension). Over the course of the hydrazine extension, 782 additional grams of water were added to the dispersion. After four days, 150 grams of an 80/20 water/Stabaxol P200 mixture was added to the dispersion.

Example 4

Prepolymer Step

The following materials were charged to a reactor: 1963 grams (1.29 equivalent) S1040-35; then with mixing, 432 grams (4.11 equivalent) TMDI and 42 grams (0.38 equivalent) of IPDI. Heat was applied to the batch to bring the temperature to over 190° F. After about 2 hours, 243 grams Santicizer 160 and 83 grams DMPA (1.2 equivalent) were added with mixing, and the prepolymer was allowed to react for approximately 2½ hours at over 190° F. An additional 237 grams of Santicizer 160 was then added to the prepolymer. The % NCO remaining then was measured and found to be 2.24%. The batch was cooled to 190° F. TEA (76 grams) was charged to the batch and allowed to mix for about 10 minutes.

Extension Step

A portion (2762 grams) of this completed, neutralized prepolymer was then charged slowly into 3261 grams of water (at 81° F.), which contained 27 grams Pluronic F68-LF surfactant, over the course of about 24 minutes, thus forming an NCO terminated prepolymer dispersion. After mixing the dispersion about 50 minutes, 41 grams of 35 wt. % hydrazine solution was slowly added (for chain extension). About 295 grams of water was added after chain extension.

Example 5

Prepolymer Step

The following materials were charged to a reactor; 2005 grams (1.22 equivalent) 67-3000HNA and 90 grams (0.20 equivalent) 67-1000HNA; then with mixing, 612 grams (5.5 equivalent) IPDI was charged. Heat was applied to bring the temperature to over 200° F. After about 2 hours, 248 grams Santicizer 160 plasticizer and 99 grams (1.5 equivalent) DMPA were added, and the batch was held at over 195° F. for about 90 minutes. An additional 248 grams Santicizer 160 was then added to the prepolymer batch. The % NCO remaining then was measured using a titration with DBA and 1.0M HCl, and was found to be 3.28%. The prepolymer was then cooled to 172° F. 82 grams of TEA was charged to the batch and allowed to mix about 10 minutes.

Extension Step

A portion (3075 grams) of this completed, neutralized prepolymer was then charged slowly into 3086 grams of water (at 72° F.), which contained 30 grams Pluronic F68-LF surfactant, over the course of about 25 minutes, thus forming an NCO terminated prepolymer dispersion. The dispersion was mixed for about 25 minutes, and then 81 grams of 35 wt. % hydrazine was added slowly, followed by 6 grams DeeFo XHD-47J defoamer.

Table 1 sets forth test data for Examples 1 to 4. In this table, "Plasticizer (wt. %)" is calculated based on the amount of plasticizer blended in the prepolymer. "Polyester soft segment (wt. %)" is calculated based upon the amount of polyester polymerized in the prepolymer, i.e., excluding plasticizer.

The data in Table 1 demonstrates that use of plasticizer allows lower 500% modulus (which for surgical gloves should be less than about 1050 psi) to be achieved while incorporating higher polyester soft segment content (Examples 1 and 4 being superior to Examples 2 and 3). Further, cracking/splitting for surgical gloves can be improved by increasing polyester soft segment content (Examples 3 and 4 being superior to Examples 1 and 2). Moroever, isopropanol resistance can be improved for surgical gloves by increasing cure temperature from about 220° F. to about 275–300° F. and by removing hydroxyl functionality (Examples 2, 3, and 4 being superior to Example 1).

Finally, increasing cure temperature also improves tensile strength, which for surgical gloves should be greater than about 2500 psi (Example 4 being superior to Examples 1, 2, and 3).

TABLE 1

| Polymer | Example 1 | Example 2 | Example 3 | Example 4 |
|---|---|---|---|---|
| Coagulant Concentration (Ca(NO$_3$)$_2$ as wt. % of dispersion) | 5% | 5% | 10% | 6% |
| Cure Time 1 (minutes) | 20 | 15 | 15 | 11 |
| Cure Temperature (° F.) | 220 | 275 | 275 | 275–300 |
| Cracking/Splitting | yes | yes | no | no |
| IPA (isopropanol) Resistance | fair | good | good | good |
| Plasticizer on Prepolymer (wt. %) | 20 | 10 | 12 | 16 |
| Polyester Soft Segment (wt. %) | 76 | 76 | 77.17 | 77.88 |
| 100% Modulus (psi) | 318 | 449 | 374 | 336 |
| 500% Modulus (psi) | 981 | 1565 | 1173 | 777 |
| Tensile Strength (psi) | 1756 | 2318 | 2162 | 3023 |
| Elongation (%) | 633 | 576 | 626 | 757 |

Example 6

Prepolymer Step

The following materials were charged to a reactor: 237 grams (0.231 equivalent) PPG-2025 and 219 grams (0.419 equivalent) PPG-1025. The mixer then was turned on, and 220 grams (1.98 equivalent) of IPDI was added to the reactor, followed by 24 grams (0.37 equivalent) DMPA and 0.050 gram of FASCAT 2003 catalyst. At this point, batch temperature was raised to over 190° F. The resultant mixture was allowed to react for two hours at 190–210° F. with nitrogen purge and good stirring. The % NCO remaining was then measured using a titration with DBA and 1.0M HCl. The finished prepolymer was cooled to 160° F., and 37 grams of Santicizer 160 was charged to the reactor. The mixture was stirred at 160° F. for 10 minutes, and the prepolymer temperature was lowered to 150° F. Then 20 grams of TEA was added to the reactor and stirred for 15 minutes. The temperature of the finished prepolymer was lowered to 140° F. for chain extension.

Extension Step 378 grams of finished prepolymer was charged slowly to a vessel containing 565 grams water at 70° F. over 8 minutes and allow to mix for 15 minutes. Chain extension was then accomplished by slowly charging 21 grams 35 wt. % hydrazine solution over an 8 minute period. After the hydrazine solution was charged, mixing was continued for 30 minutes to complete the chain extension. The result was a polymer that could be used or stored at ambient temperature.

Example 7

Prepolymer Step

The following materials were charged to a reactor: 281 grams (0.284 equivalent) PPG-2025 and 239 grams (0.458 equivalent) PPG-1025. The mixer then was turned on, and 251 grams (2.26 equivalent) of IPDI was added to the reactor, followed by 28 grams (0.42 equivalent) DMPA and 0.0150 gram FASCAT 2003 catalyst. At this point, the batch temperature was raised to over 190° F. The resultant mixture was allowed to react for two hours at 190–210° F. with nitrogen purge and good stirring. The % NCO remaining was then measured using a titration with DBA and 1.0M HCl. The finished prepolymer was cooled to 190° F., and 600 grams of prepolymer was transferred into a new reactor, followed by charging 206 grams Firemaster BZ 54 to the reactor. The mixture was stirred at 190° F. for 20 minutes, and the prepolymer temperature was lowered to 145° F. Then 17 grams of TEA was added into the reactor, and it was stirred for 20 minutes. The temperature of the finished prepolymer was lowered to 140° F. for chain extension.

Extension Step 190 grams of finished prepolymer were slowly charged to a vessel containing 291 grams water at 70° F. and 53 grams 45% Dowfax 2A1 over an 8 minute period and allowed to continue mixing for 10 minutes. Chain extension then was accomplished by slowly charging 7 grams 35 wt. % hydrazine solution over an 8 minute period. After the hydrazine solution was charged, mixing was continued for 10 minutes to complete the chain extension. The result was a polymer that could be used or stored at ambient temperature.

Example 8

Prepolymer Step

The finished prepolymer of Example 8 was also chain extended as shown below.

Extension Step 190 grams of finished prepolymer was charged slowly to a vessel containing 264 grams water at 70° F. and 80 grams 30% SLS over an 8 minute period and allowed to mix for 10 minutes. Chain extension then was accomplished by slowly charging 7 grams 35 wt. % hydrazine solution over an 8 minute period. After the hydrazine solution was charged, mixing was continued for 10 minutes to complete the chain extension. The result was a polymer that could be used or stored at ambient temperature.

Example 9

Prepolymer Step

The following materials were charged to a reactor: 281 grams (0.284 equivalent) PPG-2025 and 239 grams (0.458 equivalent) PPG-1025. The mixer then was turned on, and 251 grams (2.26 equivalent) IPDI was added to the reactor, followed by 28 grams (0.0.42 equivalent DMPA and 0.0150 gram of FASCAT 2003 catalyst. At this point the batch temperature was raised to over 190° F. The resultant mixture was allowed to react for two hours at 190–210° F. with nitrogen purge and good stirring. The % NCO remaining was then measured using a titration with DBA and 1.0M HCl. The finished prepolymer was cooled to 190° F., and 200 grams of prepolymer was transferred into a new reactor, followed by charging 69 grams of Antiblaze TCP to the reactor. The mixture was stirred at 190° F. for 20 minutes, and the prepolymer temperature was lowered to 145° F. Then 6 grams of TEA was added to the reactor and stirred for 20 minutes. The temperature of the finished prepolymer was lowered to 140° F. for chain extension.

Extension Step 120 grams of finished prepolymer was charged slowly to a vessel containing 202 grams water at 70° F. and 15 grams IGEPAL C0630 over an 8 minute period and allowed to mix for 10 minutes. Chain extension then was accomplished by slowly charging 7 grams 35 wt. % hydrazine solution over an 8 minute period. After the hydrazine solution was charged, mixing was continued for 10 minutes to complete the chain extension. The result was a polymer that could be used or stored at ambient temperature.

Example 10

Prepolymer Step

The finished prepolymer of Example 8 was also chain extended as shown below.

Extension Step 120 grams of finished prepolymer was charged slowly to a vessel containing 202 grams water at 70° F. and 34 grams 45% DOWFAX 2A1 over an 8 minute period and allowed to continue mixing for 10 minutes. Chain extension then was accomplished by slowly charging 7 grams 35 wt. % hydrazine solution over an 8 minute period. After the hydrazine solution was charged, mixing was continued for 10 minutes to complete the chain extension. The result was a polymer that could be used or stored at ambient temperature.

Example 11

Prepolymer Step

The following materials were charged to a reactor: 281 grams (0.284 equivalent) PPG-2025 and 239 grams (0.458 equivalent) PPG-1025. The mixer then was turned on, and 251 grams (2.26 equivalent) IPDI was added to the reactor, followed by 28 grams (0.42 equivalent) DMPA and 0.0150 gram FASCAT 2003 catalyst. At this point the batch temperature was raised to over 190° F. The resultant mixture was allowed to react for two hours at 190–210° F. with nitrogen purge and good stirring. The % NCO remaining then was measured using a titration with DBA and 1.0M HCl. The finished prepolymer was cooled to 180° F., and 400 grams of prepolymer was transferred into a new reactor, followed by charging 137 grams of Antiblaze into the reactor. The mixture was stirred at 190° F. for 20 minutes, and the prepolymer temperature was lowered to 145° F. Then 11 grams of TEA was added to the reactor, and it was stirred for 20 minutes. The temperature of the finished prepolymer was lowered to 140° F. for chain extension.

Extension Step 240 grams of finished prepolymer was slowly charged to a vessel containing 404 grams water at 70° F. and 30 grams IGEPAL C0630 over a 10 minute period and allowed to mix for 10 minutes. Chain extension then was accomplished by slowly charging 10 grams 35 wt. % hydrazine solution over a 10 minute period. After the hydrazine solution was charged, mixing was continued for 10 minutes to complete the chain extension. The result was a polymer that could be used or stored at ambient temperature.

Example 12

Prepolymer Step

The finished prepolymer of Example 8 was also chain extended as shown below.

Extension Step 240 grams of finished prepolymer was charged slowly to a vessel containing 426 grams water at 70° F. and 30 grams 45% DOWFAX 2A1 over a 10 minute period and allowed to continue mixing for 10 minutes. Chain extension then was accomplished by slowly charging 10 grams of 35 wt. % hydrazine solution over an 8 minute period. After the hydrazine solution was charged, mixing was continued for 10 minutes to complete the chain extension. The result was a polymer that could be used or stored at ambient temperature.

Example 13

Prepolymer Step

The following materials were charged to a reactor: 176 grams (0.178 equivalent) PPG-2025 and 150 grams (0.286 equivalent) PPG-1025. The mixer then was turned on, and 157 grams (1.41 equivalent) IPDI was added to the reactor, followed by 17 grams (0.26 equivalent) DMPA and 0.0150 gram FASCAT 2003 catalyst. At this point the batch temperature was raised to over 190° F. The resultant mixture was allowed to react for two hours at 190–210° F. with nitrogen purge and good stirring. The % NCO remaining then was measured using a titration with DBA and 1.0M HCl. The finished prepolymer was cooled to 165° F., and 400 grams of prepolymer was transferred into a new reactor, followed by charging 207 grams of Antiblaze 100 to the reactor. The mixture was stirred at 165° F. for 10 minutes, and the prepolymer temperature was lowered to 140° F. Then 14 grams of TEA was added to the reactor, and it was stirred for 20 minutes. The temperature of the finished prepolymer was lowered to 140° F. for chain extension.

Extension Step 330 grams of finished prepolymer was slowly charged to a vessel containing 512 grams water at 70° F. and 19 grams IGEPAL CO630 over a 10.0 minute period and allowed to continue mixing for 10 minutes. Chain extension then was accomplished by slowly charging 13 grams 35 wt. % hydrazine solution over a 10 minute period. After the hydrazine solution was charged, mixing was continued for 10 minutes to complete the chain extension. The result was a polymer that could be used or stored at ambient temperature.

Example 14

Prepolymer Step

The following materials were charged to a reactor: 176 grams (0.178 equivalent) PPG-2025 and 150 grams (0.286 equivalent) PPG-1025. The mixer then was turned on, and 157 grams (1.41 equivalent) of IPDI was added to the reactor, followed by 17 grams (0.26 equivalent) DMPA and 0.0150 gram of FASCAT 2003 catalyst. At this point, the batch temperature was raised to over 190° F. The resultant mixture was allowed to react for two hours at 190–210° F. with nitrogen purge and good stirring. The % NCO remaining was then measured using a titration with DBA and 1.0M HCl. The finished prepolymer was cooled to 195° F., followed by charging 207 grams of Antiblaze 524 to the reactor. The mixture was stirred at 165° F. for 10 minutes, and the prepolymer temperature was lowered to 140° F. Then 14 grams of TEA was added to the reactor, and it was stirred for 20 minutes. The temperature of the finished prepolymer was lowered to 140° F. for chain extension.

Extension Step 330 grams of finished prepolymer was charged slowly to a vessel containing 512 grams water at 70° F. and 13 grams IGEPAL CO630 over a 10 minute period and allowed to mix for 10 minutes. Chain extension then was accomplished by slowly charging 14 grams 35 wt. % hydrazine solution over a 10 minute period. After the hydrazine solution was charged, mixing was continued for 10 minutes to complete the chain extension. The result was a polymer that could be used or stored at ambient temperature.

Example 15

Prepolymer Step

The following materials were charged to a reactor: 176 grams (0.178 equivalent) PPG-2025 and 150 grams (0.286 equivalent) PPG-1025. The mixer then was turned on, and 157 grams (1.41 equivalent) of IPDI was added to the reactor, followed by 17 grams (0.26 equivalent) DMPA and 0.0150 gram FASCAT 2003 catalyst. At this point the batch temperature was raised to over 190° F. The resultant mixture was allowed to react for two hours at 190–210° F. with nitrogen purge and good stirring. The % NCO remaining then was measured using a titration with DBA and 1.0M HCl. The finished prepolymer was cooled to 195° F., followed by charging 207 grams of Antiblaze TXP to the reactor. The mixture was stirred at 165° F. for 10 minutes, and the prepolymer temperature was lowered to 140° F. Then 14 grams of TEA was added to the reactor, and it was stirred for 20 minutes. The temperature of the finished prepolymer was lowered to 140° F. for chain extension.

Extension Step 330 grams of finished prepolymer was charged slowly to a vessel containing 512 grams water at 70° F. and 13 grams IGEPAL CO630 over a 10 minute period and allowed to continue mixing for 10 minutes. Chain extension then was accomplished by slowly charging 14 grams 35 wt. % hydrazine solution over a 10 minute period. After the hydrazine solution was charged, mixing was continued for 10 minutes to complete the chain extension. The result was a polymer that could be used or stored at ambient temperature.

Example 16

Prepolymer Step

The following materials were charged to a reactor: 2397 grams (1.46 equivalent) 67-3000HNA and 125 grams (1.87 equivalent) DMPA. The mixer then was turned on, and 664 grams (5.44 equivalent) of TMXDI was added to the reactor, followed by 113 grams (1.02 equivalent) IPDI. At this point the batch temperature was raised to over 200° F. The resultant mixture was allowed to react for 90 minutes at 215–225° F. with nitrogen purge and good stirring. The % NCO remaining then was measured using a titration with DBA and 1.0M HCl. The finished prepolymer was cooled to 180° F., and 1650 grams prepolymer was transferred to a new reactor, followed by charging 427 grams of Santicizer 160 to the reactor. The mixture was stirred at 180° F. for 20 minutes, and the prepolymer temperature was lowered to 150° F. Then 57 grams of TEA was added into the reactor, and it was stirred for 15 minutes. The temperature of the finished prepolymer was lowered to 150° F. for chain extension.

Extension Step 1900 grams of finished prepolymer was charged slowly to a vessel containing 2485 grams water at 70° F. and 69 grams IGEPAL CO630 over a period of 12 minutes and allowed to continue mixing for 10 minutes. Chain extension then was accomplished by slowly charging 60 grams 35 wt. % hydrazine solution over a 12 minute period. After the hydrazine solution was charged, mixing was continued for 10 minutes to complete the chain extension. The result was a polymer that could be used or stored at ambient temperature.

Example 17

Prepolymer Step

The following materials were charged to a reactor: 369 grams (1.44 equivalent) 67-500HNA and 660 grams (2.33 equivalent) STEPANOL PD-200LV. The mixer then was turned on, and 1456 grams (11.1 equivalent) of Desmodur W was added to the reactor. The mixture was allowed to exotherm to 230–240° F. for 15 minutes and then cooled to 215–220° F. Then 23 grams TMP (0.52 equivalent) and 0.015 gram FASCAT 2003 catalyst were charged to the reactor. The reactants were stirred for 15 minutes and cooled to 210° F. The % NCO remaining then was measured using a titration with DBA and 1.0M HCl. 131 grams (1.96 equivalent) DMPA and 660 grams NMP, followed by 0.020 gram of FASCAT 2003 catalyst, were charged to the reactor. The resultant mixture was allowed to react for 60 minutes at 210° F. with nitrogen purge and good stirring. The % of NCO remaining then was measured using a titration with DBA and 1.0M HCl. The finished prepolymer was cooled to 165° F., and 1500 grams prepolymer was transfer separated for the following step. 60 grams of TATM was charged to the reactor. The mixture was stirred at 160° F. for 20 minutes, and the prepolymer temperature was lowered to 145° F. Then 42 grams TEA was added to the reactor, and it was stirred for 10 minutes. The temperature of the finished prepolymer was lowered to 140° F. for chain extension.

Extension Step 1500 grams of finished prepolymer was charged slowly to a vessel containing 1850 grams water at 70° F., 181 grams DPM and 2 grams Dehydran 1293 over a 20 minute period and allowed to continue mixing for 15 minutes. Chain extension then was accomplished by slowly charging a blend containing 48 grams 35 wt. % hydrazine solution, 22 grams ethylene diamine, and 22 grams water over a 25 minute period. After the blended solution was charged, mixing was continued for 30 minutes to complete the chain extension. The result was a polymer that could be used or stored at ambient temperature.

Example 18

Prepolymer Step

The following materials were charged to a reactor: 108 grams (0.42 equivalent) 67-500HNA and 50 grams (0.099 equivalent) 50-1000PMA. The mixer then was turned on and 223 grams (1.70 equivalent) of Desmodur W was added to the reactor. The mixture was allowed to exotherm to 230–240° F. for 15 minutes and then cooled to 215–220° F. Then 4 grams TMP (0.08 equivalent) and 0.015 gram FASCAT 2003 catalyst were charged. The reactants were stirred for 15 minutes and cooled to 210° F. The % NCO remaining then was measured using a titration with DBA and 1.0M HCl. 20 grams (0.30 equivalent) DMPA and 101 grams NMP followed by 0.030 gram of FASCAT 2003 catalyst were charged to the reactor. The resultant mixture was allowed to react for 60 minutes at 210° F. with nitrogen purge and good stirring. The percent of NCO remaining was then measured using a titration with DBA and 1.0M HCl. The finished prepolymer was cooled to 145° F., and 256.04 grams of prepolymer was transferred into a new reactor. 21 grams of TATM was charged to the reactor. The mixture was stirred at 145° F. for 5 minutes, and the prepolymer temperature was lowered to 145° F. Then 14 grams of TEA was added to the reactor, and it was stirred for 10 minutes. The temperature of the finished prepolymer was adjusted to 145° F. for chain extension.

Extension Step 200 grams of finished prepolymer was charged slowly to a vessel containing 374 grams water at 70° F., 29 grams DPM and 0.29 gram of Dehydran 1293 over a 7 minute period and allowed to mix for 10 minutes. Chain extension then was accomplished by slowly charging a blend containing 7 grams 35 wt. % hydrazine solution, 4 grams ethylene diamine, and 4 grams water over an 8 minute period. After the blended solution was charged, mixing was continued for 10 minutes to complete the chain extension. The result was a polymer that could be used or stored at ambient temperature.

Example 19

Prepolymer Step

The following material was charged to a reactor: 251 grams (0.978 equivalent) 67-500HNF. The mixer then was turned on and 351 grams (2.68 equivalent) of Desmodur W was added to the reactor. The mixture was allowed to exotherm to 230–240° F. for 15 minutes and then cooled to 215–220° F. Then 6 grams TMP (0.13 equivalent) and 0.03 gram FASCAT 2003 catalyst were charged. The reactants were stirred for 15 minutes and cooled to 210° F. The % NCO remaining then was measured using a titration with (DBA and 1.0M HCl. 32 grams (0.47 equivalent) DMPA and 160 grams NMP, followed by 0.040 gram of FASCAT 2003 catalyst were charged to the reactor. The resultant mixture was allowed to react for 60 min at 210° F. with nitrogen purge and good stirring. The % NCO remaining then was measured using a titration with DBA and 1.0M HCl. The finished prepolymer was cooled to 175° F., and 400 grams of prepolymer was transferred into a new reactor. 53 grams of TATM was charged to the reactor. The mixture was stirred at 175° F. for 10 minutes, and the prepolymer temperature was lowered to 165° F. Then 11 grams of TEA was added to the reactor, and it was stirred for 10 minutes. The temperature of the finished prepolymer was adjusted to 160° F. for chain extension.

Extension Step 330 grams of finished prepolymer was charged slowly to a vessel containing 448.21 grams water at 70° F., 40 grams DPM and 0.40 grams of Dehydran 1293 over a period of 8 minutes and allowed to continue mixing for 10 minutes. Chain extension then was accomplished by slowly charging a blend containing 9 grams 35 wt. % hydrazine solution, 4 grams ethylene diamine, and 4 grams water over an 8 minute period. After the blended solution was charged, mixing was continued for 20 minutes to complete the chain extension. The result was a polymer that could be used or stored at ambient temperature.

Example 20

Prepolymer Step

NCO-terminated prepolymer was prepared in the prepolymer step. A one-gallon reactor was equipped with a mechanical stirrer, thermometer and nitrogen inlet. The reactor was charged with 0.45 equivalent of 67-1000 HNA, 1.5 equivalents of Desmodur W, and 0.5 equivalent of TMXDI, and then heated to 155° F. After 10 minutes of mixing at 155° F., 0.55 equivalent of DMPA was added to the mixture with good mixing, followed by three drops of FASCAT® 2003 catalyst. The resultant mixture was allowed to react for about two hours at 220° F. Then 10% of K-Flex® DP based on prepolymer weight was charged as diluent and mixed another 30 minutes at this temperature. The unreacted % NCO of the prepolymer was then determined by withdrawing a known amount of sample from reactor and titrating against DBA, followed by 1.0M HCl. The reaction mixture then was allowed to cool to 165° F. Prepolymer was neutralized by mixing thoroughly with 1.01 equivalents of TEA at about 160° F. The Brookfield viscosity of the neutralized polymer was measured as 1995 mPa.s at 161° F.

Extension Step

Dispersion was carried out by charging 1150 grams of neutralized prepolymer into a vessel containing 2285 grams of water at 60° F. with rapid mixing. Chain extension was carried out with slow addition of 35 wt. % diluted hydrazine (0.85 equivalent) for 15 to 30 minutes to obtain a dispersion from which a polyurethane film could be made having lower modulus than if K-Flex® DP had not been employed as a plasticizer. The dispersion had these properties: total solids= 32 wt. %, viscosity=12.5 mPa.s, and pH=7.25.

Example 21

Prepolymer Step

Example 20 was repeated with 10% diethylene glycol dibenzoate ester (K-Flex® DE) as diluent. A slightly high viscosity neutralized prepolymer was obtained (30,000 mPa.s at 160° F.).

Extension Step

The extension procedure was followed as in Example 20 to obtain a dispersion from which a polyurethane film could be made having lower modulus than if K-Flex® DE had not been employed as a plasticizer. The dispersion had these properties: total solids=32 wt. %, viscosity=22.5 mPa.s, and pH=7.56.

Example 22

Prepolymer Step

Example 20 was repeated with 10% K-Flex® 500, which is a blend of K-Flex® DE and K-Flex® DP, as diluent. The prepolymer was neutralized by mixing thoroughly with 1.01 equivalents of DMEA at about 160° F. The Brookfield viscosity of neutralized prepolymer was 15,400 mPa.s at 160° F.

Extension Step

A dispersion was made by charging 1260 grams of neutralized prepolymer into a vessel containing 2294 grams of water at 60° F. with rapid mixing. Chain extension was completed with slow addition of 35 wt. % diluted hydrazine (0.85 equivalent) for 15 to 30 minutes to obtain a dispersion from which a polyurethane film could be made having lower modulus than if K-Flex® 500 had not been employed as a plasticizer. The result was a dispersion having these properties: total solids 36.1 wt. %, viscosity=47.5 mPa.s, and pH=8.62.

Tensile strength, % elongation and 100% modulus test results for Examples 20–22 are reported in Table 2. The compositions of Examples 20–22 (which have higher modulus than Examples 1–4) are useful in non-glove applications such as personal care products.

TABLE 2

|  | Example 20 | Example 21 | Example 22 |
|---|---|---|---|
| 100% modulus (psi) | 3021 | 3202 | 3414 |
| Tensile at max load (psi) | 4461 | 5075 | 3965 |
| Elongation at break (%) | 255.7 | 283.9 | 201 |

Example 23

Prepolymer Step

Example 20 was repeated to make plasticizer-free chain-extended prepolymer for comparison with the plasticized chain-extended prepolymer of Example 20 and the sunscreen lotion of Example 24 as shown in Table 4.

A one-quart reactor was charged with 0.45 equivalent 67-1000HNA, 1.5 equivalents Desmodur W, and 0.5 equivalent TMXDI, and then heated to 155° F. After 10 minutes of mixing at 155° F., 0.55 equivalent DMPA was added to the mixture with good mixing, followed by three drops FASCAT® 2003 catalyst. The resultant mixture was allowed to react for about two hours at 220° F. The % NCO remaining then was measured using a titration with DBA and 1.0M HCl. The reaction mixture then was allowed to cool to 180° F. The prepolymer was neutralized by mixing thoroughly with 1.01 equivalents TEA at about 180° F. The Brookfield viscosity of the neutralized prepolymer without NMP was measured as 70,500 mPa.s at 180° F.

Extension Step

Dispersion was carried out by charging 400 grams of neutralized prepolymer into a vessel containing 682 grams water at about 50–60° F. with rapid mixing. Dispersion was difficult to achieve because of high prepolymer viscosity. Chain extension was carried out with slow addition of 35 wt. % diluted hydrazine (0.85 equivalent) for 15 to 30 minutes to obtain an extended dispersion having these properties: total solids=30.3 wt. %, viscosity=20.5 mPa.s, and pH=7.8.

Example 24

Sunscreen Lotion

A sunscreen lotion was prepared having the composition shown in Table 3 below, including the chain-extended polymer prepared in Example 20. Part A ingredients were combined and mixed until homogenous. The first four ingredients of Part B were combined in a separate vessel and mixed using moderate agitation with heat until the oxybenzone dissolved. The Part B mixture was cooled to 45° C., and then Pemulen TR-2 was added with continued mixing. With vigorous agitation, Part B was added to Part A until a smooth, non-grainy dispersion was achieved. AMP-95 was added to the mixture, and mixing was continued for about one hour. All mixing was moderate, i.e., 800–1200 rpm using a Caframo mixer and a marine propeller mixing blade. Film forming polymer and fragrance were added to the batch and mixed until uniform.

TABLE 3

| Ingredients | Wt. % | Function |
|---|---|---|
| Part A | | |
| Deionized water | 66.46 | Diluent |
| Carbopol ® Ultrez ™ 10 | 0.25 | Thickener |
| Methocel ® E4M | 0.1 | Spreading aid |
| Propylene glycol | 1.0 | Humectant |
| Nuosept ™ C | 0.4 | Preservative |
| Disodium EDTA | 0.05 | Chelator |
| Crovol ™ A-40 | 0.4 | Particle size reducer |
| Part B | | |
| Neo Helipan ™ Type AV | 7.5 | UV absorber |
| Octyl salicylate | 5.0 | UV absorber |
| Neo Helipan ™ Type BB | 6.0 | UV absorber |
| Drakeol 21 | 5.0 | Emollient |
| Pemulen TR-2 | 0.25 | Emulsifier |
| Part C | | |
| AMP-95 | 0.3 | Neutralizer |
| Example 20 chain-extended polymer dispersion | 7.5 | Film former |
| Fragrance #99189 "Twister" | 0.15 | Fragrance |

Comparative UV radiation screening, or UV radiation screening enhancement capabilities of the Example 20 plasticized chain extended polyurethane dispersion, the Example 23 plasticizer-free chain-extended polyurethane dispersion, and the Example 24 sunscreen lotion are reported in Table 4. The transmittance spectrum of the Example 24 sunscreen lotion showed complete absorbence (or 0% transmittance) from 200 to 320 nm, except for a small peak of about 10% transmittance at 260 nm.

TABLE 4

| Example # | $\lambda_{max}$ | Concentration (Wt. %) | Absorbence (%) | Transmittance (%) |
|---|---|---|---|---|
| Example 20 (plasticized chain-extended prepolymer dispersion) | 203, 232[1] | 0.013 wt. % in ethanol | 2.6 | 0 |
| Example 23 (plasticizer-free chain-extended prepolymer dispersion) | 203 | 0.013 wt. % in ethanol | 2.6 | 0 |
| Example 24 (sunscreen lotion) | — | — | — | See footnote 2 |

[1]The plasticizer produced two absorption peaks at 203 and 232 nm.
[2]The transmittance spectrum of the sunscreen lotion showed complete absorbence (or 0% transmittance) from 200 to 320 nm, except for a small peak of about 10% transmittance at 260 nm.

Example 25

Moisture Resistant Film in Hair Care Formulation

Three "hair gel" formulations were blended using the ingredients listed in Table 5. The Carbopol® 980 was dispersed in water with vigorous agitation until a smooth, non-grainy dispersion was achieved. Triethanolamine (99 wt. % in water) was added to the mixture until the desired pH (listed in Table 5) was achieved, and mixing was continued for about one hour. All mixing was moderate, i.e., 800–1200 rpm using a Caframo mixer and a marine propeller mixing blade. Film forming polymer was added to the batch and mixed until homogeneous.

TABLE 5

| Ingredient | Amount (Control 1) | Amount | Amount | Ingredient Function |
|---|---|---|---|---|
| Film forming polymer | 3 wt. % of Luviskol VA64 | 1 wt. % of Example 20 plasticized chain-extended prepolymer dispersion | 1 wt.% of Example 23 plasticizer-free chain-extended prepolymer dispersion | Fixative |
| Water | To 100 wt. % | To 100 wt. % | To 100 wt. % | Diluent |
| Cabopol® 980 | 0.5 wt. % | 0.5 wt. % | 0.5 wt. % | Thickener |
| Triethanolamine[1] | To pH 6.01 | To pH 7.1 | To pH 7.1 | Neutralizer |

[1]99 wt. % solution in water

Example 26

Comparative Hair Styling Tests

The ability of the plasticized chain-extended prepolymer dispersion of Example 20 to perform in a hair fixative/styling gel (made as shown in Table 5 and having improved moisture resistance) was measured by hair curl retention, compared to Example 23 plasticizer-free chain-extended prepolymer dispersion in a hair fixative/styling gel (made as shown in Table 5). Comparison also was made to two commercially available hair fixative/styling gels and to Control 1 (made as shown in Table 5). Satisfactory curl retention typically is at least 70% curl retention for at least 2 hours at 90% relative humidity.

Test results in Table 6 show superior performance of the Example 20 dispersion in a hair gel formulation for at least 6 hours. In sharp contrast, the three controls and the Example 23 plasticizer-free dispersion in a hair gel formulation all dropped below the required 70% curl retention in less than 4 hours.

TABLE 6

| Example | Film Forming Polymer | Solids, Wt. % | 70% Curl Retention Time |
|---|---|---|---|
| Control 1 | Luviskol VA64 | 3 | <1 hr |
| Control 2 | Paul Mitchell Max Hold | — | <4 hr |
| Control 3 | Nexxus Regular Hold | — | <1 hr |
| Example 23 | Example 23 dispersion in hair gel formulation | 1 | 3 hr |
| Example 20 | Example 20 dispersion in hair gel formulation | 1 | 6 hr |

Example 27

Prepolymer Step

The following materials were charged to a reactor: 303 grams 1000-DEA (hydroxyl number=112.9), 301 grams Desmodur-W, 36 grams DMPA and 160 grams butylbenzylphthalate plasticizer. They were stirred at 93 to 99° C.

over 3 hours and then cooled to 60° C. 700 grams of the mixture was dispersed with agitation into 1120 grams water containing 27 grams TEA.

Extension Step

After stirring the dispersion for an additional 20 minutes, 36 grams of 35 wt. % hydrazine solution was added over a period of 5 minutes. The result was a dispersion having these properties: total solids=43 wt. %, pH=7.8, and average particle size=155 nm. The properties of a film formed from this dispersion are reported in Table 7.

Example 28

Prepolymer Step

This comparative example illustrates preparation of a polymer using NMP but without plasticizer. The following materials were charged to a reactor: 274 grams 1000-DEA, 321 grams Desmodur-W, 45 grams DMPA and 112 grams NMP. They were stirred at 93 to 99° C. over a 3-hour period and then cooled to 60° C. An additional 47 grams NMP was added, and 700 grams of the mixture was dispersed with agitation into 1138 grams water containing 34 grams TEA.

Extension Step

After stirring the dispersion for additional 20 minutes, 36 grams of 35 wt. % hydrazine solution in water was added over a period of 5 minutes. The dispersion had the following properties: total solids=37 wt. %, pH=7.6, and average particle size=35 nm.

Film property data (using Test Method 2 described heretofore) is reported in Table 7 for films formed from the polymer dispersions made in Examples 27 and 28. Retained tensile strength is reported as a percentage of initial film tensile strength and is calculated by dividing initial film tensile strength into tensile strength of either (a) the film after hydrolysis chamber exposure, or (b) the film formed from the aged polymer dispersion, and then multiplying the quotient by 100. Retained elongation is reported as a percentage of initial elongation % and is calculated by dividing initial elongation into elongation % of either (a) the film after hydrolysis chamber exposure, or (b) the film formed from the aged polymer dispersion, and then multiplying the quotient by 100.

Table 7 shows superior hydrolytic stability (measured as retained % tensile strength and retained % elongation) of a film formed from the Example 27 polymer (which was made using a plasticizer but without NMP), compared to a film formed from the Example 28 polymer (which was made using NMP that volatilized during film formation). Table 7 also shows superior aging stability (measured as retained % tensile strength and retained % elongation) of a film formed from the Example 27 polymer dispersion (which was made using a plasticizer but without NMP and thereafter aged for 1 year at ambient temperature), compared to a film formed from the Example 28 polymer dispersion (which was aged under the same conditions as Example 27 and made using NMP that volatilized during film formation).

TABLE 7

|  |  | Example 27 | Example 28 |
|---|---|---|---|
| Initial film properties | Tensile strength at max load (psi) | 3920 | 9350 |
|  | Elongation at break (%) | 515 | 575 |
| Film properties after 1 day in hydrolysis chamber at 95% humidity and 75° C. | Tensile strength at max load (psi) | 3050 | 3070 |
|  | Retained tensile strength (%) | 78 | 33 |
|  | Elongation at break (%) | 530 | 84 |
|  | Retained elongation (%) | 103 | 15 |
| Film properties after 1-year aging of dispersion at ambient temperature | Tensile strength at max load (psi) | 3070 | 5840 |
|  | Retained tensile strength (%) | 78 | 62 |
|  | Elongation at break (%) | 535 | 370 |
|  | Retained elongation (%) | 104 | 64 |

While in accordance with the patent statutes the best mode and preferred embodiment has been set forth, the scope of the invention is not limited thereto, but rather by the scope of the attached claims.

What is claimed is:

1. A polyurethane dispersion that is the product of a process comprising:
    (a) reacting (1) at least one polyisocyanate having an average of about two or more isocyanate groups, and (2) at least one active hydrogen containing compound selected from polyester polyols, polycarbonate polyols, polysiloxane polyols, ethoxylated polysiloxane polyols, and mixtures thereof, and (3) at least one water dispersability enhancing compound having at least one hydrophilic, ionic or potentially ionic group in order to form an isocyanate terminated prepolymer; wherein an effective amount of at least one plasticizer is introduced into the reaction at any time during prepolymer formation; and
    (b) subsequently (1) dispersing said prepolymer in water, and (2) chain extending said prepolymer by reaction with at least one of water, inorganic or organic polyamine having an average of about 2 or more primary and/or secondary amine groups, or combinations thereof.

2. A polyurethane dispersion of claim 1 wherein the amount of organic diluents or solvents is less than about 20 wt. % of the total weight of said prepolymer.

3. A polyurethane dispersion of claim 2 wherein the amount of said organic diluents and solvents is less than about 15 wt. % of the total weight of said prepolymer.

4. A polyurethane dispersion of claim 3 wherein the amount of said other organic diluents and solvents is less than about 10 wt. % of the total weight of said prepolymer.

5. A polyurethane dispersion of claim 4 wherein the amount of said other organic diluents and solvents is less than about 5 wt. % of the total weight of said prepolymer.

6. A polyurethane dispersion of claim 5 wherein said process occurs in the complete absence of organic diluents or solvents other than said plasticizer.

7. A polyurethane dispersion of claim 1 wherein said water dispersability enhancing compound is derived from a hydroxy-carboxylic acid.

8. A polyurethane dispersion of claim 7 wherein said reaction step (b) includes neutralization of said prepolymer.

9. A polyurethane dispersion of claim 8 wherein said neutralization is performed using a tertiary amine comprising at least one of triethylamine, dimethylethanolamine, or N-methylmorpholine, or combinations thereof.

10. A polyurethane dispersion of claim 7 wherein said water dispersability enhancing compound is used in an amount up to about 30 wt. % based on the total weight of said prepolymer.

11. A polyurethane dispersion of claim 10 where said reaction step (b) includes neutralization of said prepolymer.

12. A polyurethane dispersion of claim 7 wherein said water dispersability enhancing compound has the formula $(HO)_xQ(COOH)_y$ wherein Q is a straight or branched chain radical containing 1 to 12 carbon atoms, and x and y are 1 to 3.

13. A polyurethane dispersion of claim 11 wherein said prepolymer has an acid number from 6 to 60.

14. A polyurethane dispersion of claim 12 wherein said water dispersability enhancing compound is dimethylolpropanoic acid.

15. A polyurethane dispersion of claim 7 where said water dispersability enhancing compound comprises at least one of dimethylolpropanoicacid, tartaric acid, dimethylol butanoic acid, glycolic acid, thioglycolic acid, lactic acid, malic acid, dihydroxymalic acid, dihydroxytartaric acid, 2,6-dihydroxybenzoic acid, sulfoisophthalic acid, or combinations thereof.

16. A polyurethane dispersion of claim 1 wherein said polyisocyanate has an average of about 2 to 4 isocyanate groups and comprises at least one aliphatic polyisocyanate, aromatic polyisocyanate, cycloaliphatic polyisocyanate, or araliphatic polyisocyanate, or combinations thereof.

17. A polyurethane dispersion of claim 16 wherein said polyisocyanate comprises at least one of isophorone diisocyanate, 2,2,4-trimethyl-1,6-hexamethylene diisocyanate, 2,4,4-trimethyl-1,6-hexamethylene diisocyanate, tetramethylxylylene diisocyanate, methylene bis-(4-cyclohexyl isocyanate), or methylene bis-(4-phenyl isocyanate), toluene diisocyanate, or combinations thereof.

18. A polyurethane dispersion of claim 16 wherein said polyester polyol comprises at least one of hexanediol neopentyl adipate, ethylene glycol/diethylene glycol adipate, or ethylene glycol/butane diol adipate, or combinations thereof.

19. A polyurethane dispersion of claim 1 wherein said polyamine comprises at least one of diethylenetriamine, ethylenediamine, meta-xylylenediamine, aminoethyl ethanolamine, or hydrazine, or combinations thereof.

20. A polyurethane dispersion of claim 1 wherein said plasticizer comprises at least one flame retardant plasticizer.

21. A polyurethane dispersion of claim 20 wherein said flame retardant plasticizer comprises at least one of cyclic phosphate ester, cresol phosphate, xylyl phosphate, phenol phosphate, chloro alkyl diphosphate ester, trixylyl phosphate, halogenated aryl ester, or combination thereof.

22. A polyurethane dispersion of claim 1 where said plasticizer comprises a reactive plasticizer.

23. A polyurethane dispersion of claim 22 wherein said reactive plasticizer has ethylenic unsaturation.

24. A polyurethane dispersion of claim 23 wherein said reactive plasticizer comprises triallyl trimellitate.

25. A polyurethane dispersion of claim 1 wherein said plasticizer comprises one or more of diethylene glycol dibenzoate ester; dipropylene glycol dibenzoate ester; butyl phenylmethyl ester of 1,2-benzenedicarboxylic acid; n-butyl benzyl ester of o-phthalic acid; a polyester diol reaction product of o-phthalic acid and diethylene glycol; a polyester diol reaction product of propylene glycol, maleic anhydride, and adipic acid; a polyester diol reaction product of hexane diol, neopentyl glycol, and adipic acid; a polyester diol reaction product of hexane diol, neopentyl glycol, and adipic acid; a polyester diol reaction product of hexane diol, neopentyl glycol, and fumaric acid; or combinations thereof.

26. A polyurethane dispersion of claim 1 wherein the NCO to active hydrogen ratio of the prepolymer is about 1.4/1 to about 2/1.

27. A polyurethane dispersion of claim 26 wherein the NCO to active hydrogen ratio of the prepolymer is about 1.5/1 to about 1.8/1.

28. A polyurethane dispersion of claim 1 wherein said dispersion is processed further to form a film.

29. A polyurethane dispersion of claim 28 wherein said film is a glove.

30. A polyurethane dispersion of claim 1 wherein said dispersion is processed further to form a personal care product.

31. A polyurethane dispersion of claim 30 wherein said personal care product is a sunscreen lotion.

32. A polyurethane dispersion of claim 30 wherein said personal care product is a hair care formulation.

33. A process for producing a polyurethane dispersion, said process comprising:
    (a) reacting (1) at least one polyisocyanate having an average of about two or more isocyanate groups, (2) at least one active hydrogen containing compound selected from polyester polyols, polycarbonate polyols, polysiloxane polyols, ethoxylated polysiloxane polyols, and mixtures thereof, and (3) at least one water dispersability enhancing compound having at least one hydrophilic, ionic or potentially ionic group in order to form an isocyanate terminated prepolymer; wherein an effective amount of at least one plasticizer is introduced into the reaction at any time during prepolymer formation; and
    (b) subsequently (1) dispersing said prepolymer in water, and (2) chain extending said prepolymer by reaction with at least one of water, inorganic or organic polyamine having an average of about 2 or more primary and/or secondary amine groups, or combinations thereof.

34. A process of claim 33 wherein the amount of organic diluents and solvents is less than about 20 wt. % of the total weight of said prepolymer.

35. A process of claim 34 wherein the amount of said organic diluents and solvents is less than about 15 wt. % of the total weight of said prepolymer.

36. A process of claim 35 wherein the amount of said organic diluents and solvents is less than about 10 wt. % of the total weight of said prepolymer.

37. A process of claim 36 wherein the amount of said organic diluents and solvents is less than about 5 wt. % of the total weight of said prepolymer.

38. A process of claim 37 wherein said process occurs in the complete absence of organic diluents or solvents other than said plasticizer.

39. A process of claim 33 wherein said water dispersability enhancing compound is derived from a hydroxycarboxylic acid.

40. A process of claim 39 wherein said reaction step (b) includes neutralization of said prepolymer.

41. A process of claim 40 wherein said neutralization is performed using a tertiary amine comprising at least one of triethylamine, dimethylethanolamine, or N-methylmorpholine, or combinations thereof.

42. A process of claim 39 wherein said water dispersability enhancing compound is used in an amount up to about 30 wt. % based on the total weight of said prepolymer.

43. A process of claim 42 where said reaction step (b) includes neutralization of said prepolymer.

44. A process of claim 39 wherein said water dispersability enhancing compound has the formula $(HO)_xQ(COOH)_y$ wherein Q is a straight or branched chain radical containing 1 to 12 carbon atoms, and x and y are 1 to 3.

45. A process of claim 33 wherein said prepolymer has an acid number from 6 to 60.

46. A process of claim 44 wherein said water dispersability enhancing compound is dimethylolpropanoic acid.

47. A process of claim 39 where said water dispersability enhancing compound comprises at least one of dimethylolpropanoic acid, tartaric acid, dimethylol butanoic acid, glycolic acid, thioglycolic acid, lactic acid, malic acid, dihydroxymalic acid, dihydroxytartaric acid, 2,6-dihydroxybenzoic acid, sulfoisophthalic acid, or combinations thereof.

48. A process of claim 33 wherein said polyisocyanate has an average of about 2 to 4 isocyanate groups and comprises at least one aliphatic polyisocyanate, aromatic polyisocyanate, cycloaliphatic polyisocyanate, or araliphatic polyisocyanate, or combinations thereof.

49. A process of claim 48 wherein said polyisocyanate comprises at least one of isophorone diisocyanate, 2,2,4-trimethyl-1,6-hexamethylene diisocyanate, 2,4,4-trimethyl-1,6-hexamethylene diisocyanate, tetramethylxylylene diisocyanate, methylene bis-(4-cyclohexyl isocyanate), or methylene bis-(4-phenyl isocyanate), toluene diisocyanate, or combinations thereof.

50. A process of claim 48 wherein said polyester polyol comprises at least one of hexanediol neopentyl adipate, ethylene glycol/diethylene glycol adipate, or ethylene glycol/butane diol adipate, or combinations thereof.

51. A process of claim 33 wherein said polyamine comprises at least one of diethylenetriamine, ethylenediamine, meta-xylylenediamine, aminoethyl ethanolamine, or hydrazine, or combinations thereof.

52. A process of claim 33 wherein said plasticizer comprises at least one flame retardant plasticizer.

53. A process of claim 52 wherein said flame retardant plasticizer comprises at least one of cyclic phosphate ester, cresol phosphate, xylyl phosphate, phenol phosphate, chloro alkyl diphosphate ester, trixylyl phosphate, halogenated aryl ester, or combination thereof.

54. A process of claim 33 where said plasticizer comprises a reactive plasticizer.

55. A process of claim 54 wherein said reactive plasticizer has ethylenic unsaturation.

56. A process of claim 55 wherein said reactive plasticizer comprises triallyl trimellitate.

57. A process of claim 33 wherein said plasticizer comprises one or more of diethylene glycol dibenzoate ester; dipropylene glycol dibenzoate ester; butyl phenylmethyl ester of 1,2-benzenedicarboxylic acid; n-butyl benzyl ester of o-phthalic acid; a polyester diol reaction product of o-phthalic acid and diethylene glycol; a polyester diol reaction product of propylene glycol, maleic anhydride, and adipic acid; a polyester diol reaction product of hexane diol, neopentyl glycol, and adipic acid; a polyester diol reaction product of hexane diol, neopentyl glycol, and adipic acid; a polyester diol reaction product of hexane diol, neopentyl glycol, and fumaric acid; or combinations thereof.

58. A process of claim 33 wherein the NCO to active hydrogen ratio of the prepolymer is about 1.4/1 to about 2/1.

59. A process of claim 58 wherein the NCO to active hydrogen ratio of the prepolymer is about 1.5/1 to about 1.8/1.

60. A process of claim 33 wherein said dispersion is processed further to form a film.

61. A process of claim 60 wherein said film is a glove.

62. A process of claim 33 wherein said dispersion is processed further to form a personal care product.

63. A process of claim 62 wherein said personal care product is a sunscreen lotion.

64. A process of claim 62 wherein said personal care product is a hair care formulation.

65. A personal care composition comprising a topically acceptable phase, together with a polyurethane dispersion that is the product of a process comprising:
(a) reacting (1) at least one polyisocyanate having an average of about two or more isocyanate groups, (2) at least one active hydrogen containing compound selected from polyester polyols, polycarbonate polyols, polysiloxane polyols, ethoxylated polysiloxane polyols, and mixtures thereof, and (3) at least one water dispersability enhancing compound having at least one hydrophilic, ionic or potentially ionic group in order to form an isocyanate terminated prepolymer; wherein from about 5 to about 25 weight percent, based on the prepolymer weight, of at least one plasticizer is introduced into the reaction at any time during prepolymer formation; and
(b) subsequently (1) dispersing said prepolymer in water, and (2) chain extending said prepolymer by reaction with at least one of water, inorganic or organic polyamine having an average of about 2 or more primary and/or secondary amine groups, or combinations thereof.

66. A personal care composition of claim 65 wherein the amount of organic diluents or solvents is less than about 20 wt. % of the total weight of said prepolymer.

67. A personal care composition of claim 66 wherein the amount of said organic diluents and solvents is less than about 15 wt. % of the total weight of said prepolymer.

68. A personal care composition of claim 67 wherein the amount of said organic diluents and solvents is less than about 5 wt. % of the total weight of said prepolymer.

69. A personal care composition of claim 68 wherein the amount of said other organic diluents and solvents is less than about 5 wt. % of the total weight of said prepolymer.

70. A personal care composition of claim 69 wherein said process occurs in the complete absence of organic diluents or solvents other than said plasticizer.

71. A personal care composition of claim 65 wherein said water dispersability enhancing compound is derived from a hydroxyl-carboxylic acid.

72. A personal care composition of claim 71 wherein said reaction step (b) includes neutralization of said prepolymer.

73. A personal care composition of claim 72 wherein said neutralization is performed using a tertiary amine comprising at least one of triethylamine, dimethylethanolamine, or N-methylmorpholine, or combinations thereof.

74. A personal care composition of claim 71 wherein said water dispersability enhancing compound is used in an amount up to about 30 wt. % based on the total weight of said prepolymer.

75. A personal care composition of claim 74 where said reaction step (b) includes neutralization of said prepolymer.

76. A personal care composition of claim 71 wherein said water dispersability enhancing compound has the formula $(HO)_xQ(COOH)_y$ wherein Q is a straight or branched chain radical containing 1 to 12 carbon atoms, and x and y are 1 to 3.

77. A personal care composition of claim 76 wherein said water dispersability enhancing compound is a dihydroxycarboxylic acid and the prepolymer has an acid number from 6 to 60.

78. A personal care composition of claim 77 wherein said dihydroxycarboxylic acid is dimethylolpropanoic acid.

79. A personal care composition of claim 71 where said water-dispersability enhancing compound comprises at least one of dimethylol propanoic acid, tartaric acid, dimethylol butanoic acid, glycolic acid, thioglycolic acid, lactic acid, malic acid, dihydroxymalic acid, dihydroxytartaric acid, 2,6-dihydroxybenzoic acid, sulfoisophthalic acid, or polyethylene glycol, or combinations thereof.

80. A personal care composition of claim 65 wherein said polyisocyanate has an average of about 2 to 4 isocyanate groups and comprises at least one aliphatic polyisocyanate, aromatic polyisocyanate, cycloaliphatic polyisocyanate, or araliphatic polyisocyanate, or combinations thereof, and said active hydrogen containing compound comprises at least one polyester polyol, polyether polyol, polyhydroxy polycarbonate, polyamine, polysiloxane polyol, ethoxylated polysiloxane polyol, or combinations thereof.

81. A personal care composition of claim 80 wherein said polyisocyanate comprises at least one of isophorone diisocyanate, 2,2,4-trimethyl-1,6-hexamethylene diisocyanate, 2,4,4-trimethyl-1,6-hexamethylene diisocyanate, tetramethylxylylene diisocyanate, methylene bis-(4-cyclohexyl isocyanate), or methylene bis-(4-phenyl isocyanate), toluene diisocyanate, or combinations thereof.

82. A personal care composition of claim 80 wherein said polyester polyol comprises at least one of hexanediol neopentyl adipate, ethylene glycol/diethylene glycol adipate, or ethylene glycol/butane diol adipate, or combinations thereof.

83. A personal care composition of claim 65 wherein said polyamine comprises at least one of diethylenetriamine, ethylenediamine, meta-xylylenediamine, aminoethyl ethanolamine, or hydrazine, or combinations thereof.

84. A personal care composition of claim 65 wherein said plasticizer comprises at least one alkoxylated fatty alcohol phosphate ester.

85. A personal care composition of claim 84 wherein said plasticizer comprises at least one of oleth-2 phosphate, oleth-3 phosphate, oleth-4 phosphate, oleth-10 phosphate, oleth-20 phosphate, ceteth-8 phosphate, ceteareth-5 phosphate, ceteareth-10 phosphate, PPG ceteth-10 phosphate, or combinations thereof.

86. A personal care composition of claim 65 where said plasticizer comprises a reactive plasticizer.

87. A personal care composition of claim 86 wherein said reactive plasticizer has ethylenic unsaturation.

88. A personal care composition of claim 87 wherein said reactive plasticizer comprises triallyl trimellitate.

89. A personal care composition of claim 65 wherein said plasticizer comprises one or more of diethylene glycol dibenzoate ester; dipropylene glycol dibenzoate ester; butyl phenylmethyl ester of 1,2-benzenedicarboxylic acid; n-butyl benzyl ester of o-phthalic acid; a polyester diol reaction product of o-phthalic acid and diethylene glycol; a polyester diol reaction product of propylene glycol, maleic anhydride, and adipic acid; a polyester diol reaction product of hexane diol, neopentyl glycol, and adipic acid; a polyester diol reaction product of hexane diol, neopentyl glycol, and adipic acid; a polyester diol reaction product of hexane diol, neopentyl glycol, and fumaric acid; or combinations thereof.

90. A personal care composition of claim 65 wherein the NCO to active hydrogen ratio of the prepolymer is about 1.4/1 to about 2/1.

91. A personal care composition of claim 90 wherein the NCO to active hydrogen ratio of the prepolymer is about 1.5/1 to about 1.8/1.

92. A personal care composition of claim 65 wherein said dispersion is processed further to form a film.

93. A personal care composition of claim 92 which is a sunscreen lotion.

94. A personal care composition of claim 92 which is a hair care formulation.

* * * * *